(12) United States Patent
Fripp et al.

(10) Patent No.: US 10,677,015 B2
(45) Date of Patent: Jun. 9, 2020

(54) WELLBORE ISOLATION DEVICES WITH SLIP BANDS AND WEAR BANDS HAVING MODIFIED SURFACES

(71) Applicant: Halliburton Energy Services, Inc., Houston, TX (US)

(72) Inventors: Michael Linley Fripp, Carrollton, TX (US); John Charles Gano, Lowry Crossing, TX (US); Zachary William Walton, Carrollton, TX (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 144 days.

(21) Appl. No.: 15/763,048

(22) PCT Filed: Dec. 29, 2015

(86) PCT No.: PCT/US2015/067786
§ 371 (c)(1),
(2) Date: Mar. 23, 2018

(87) PCT Pub. No.: WO2017/116409
PCT Pub. Date: Jul. 6, 2017

(65) Prior Publication Data
US 2019/0055810 A1 Feb. 21, 2019

(51) Int. Cl.
*E21B 33/129* (2006.01)
*A61K 9/00* (2006.01)
(Continued)

(52) U.S. Cl.
CPC ........ *E21B 33/1292* (2013.01); *A61K 9/0014* (2013.01); *A61K 9/0019* (2013.01);
(Continued)

(58) Field of Classification Search
CPC . E21B 33/1292; E21B 33/128; A61K 9/0014; A61K 9/0019; A61K 9/16; A61K 33/08; A61K 47/06; A61K 47/34
See application file for complete search history.

(56) References Cited

U.S. PATENT DOCUMENTS

| 5,701,954 A | 12/1997 | Kilgore et al. |
| 6,688,400 B2 | 2/2004 | Metcalfe et al. |

(Continued)

FOREIGN PATENT DOCUMENTS

WO  WO-2013/012572 A2  1/2013

OTHER PUBLICATIONS

International Search Report and Written Opinion from PCT/US2015/067786, dated Sep. 21, 2016, 15 pages.

*Primary Examiner* — Yong-Suk Ro
(74) *Attorney, Agent, or Firm* — McGuireWoods, LLP

(57) ABSTRACT

Wellbore isolation devices may be produced with wear bands and slips having modified surfaces to change the frictional properties between these components and the surrounding wellbore surface. A wellbore isolation device may include: a mandrel; slips disposed circumferentially about the mandrel and in a first position along the mandrel. The slips comprise particles coupled thereto forming a modified surface. The particles comprise at least some sharp protrusions. At least one packer element is disposed along the mandrel and in a second position along the mandrel.

18 Claims, 4 Drawing Sheets

(51) Int. Cl.
*A61K 9/16* (2006.01)
*A61K 33/08* (2006.01)
*A61K 47/06* (2006.01)
*A61K 47/34* (2017.01)
*E21B 33/128* (2006.01)

(52) U.S. Cl.
CPC .............. *A61K 9/16* (2013.01); *A61K 33/08* (2013.01); *A61K 47/06* (2013.01); *A61K 47/34* (2013.01); *E21B 33/128* (2013.01)

(56) References Cited

U.S. PATENT DOCUMENTS

| | | |
|---|---|---|
| 8,695,714 B2 | 4/2014 | Xu et al. |
| 2011/0048743 A1 | 3/2011 | Stafford et al. |
| 2013/0048305 A1 | 2/2013 | Xu et al. |
| 2013/0327545 A1 | 12/2013 | Marya et al. |
| 2014/0190685 A1 | 7/2014 | Frazier et al. |
| 2015/0285026 A1* | 10/2015 | Frazier ................ E21B 33/1291 166/120 |

\* cited by examiner

WELLBORE ISOLATION DEVICES WITH SLIP BANDS AND WEAR BANDS HAVING MODIFIED SURFACES

BACKGROUND

The present disclosure describes embodiments of wellbore isolation devices.

In the drilling, completion, and stimulation of hydrocarbon-producing wells, a variety of downhole tools are used. For example, it is often desirable to seal portions of a wellbore, such as during fracturing operations when various fluids and slurries are pumped from the surface into a casing string that lines the wellbore, and forced out into a surrounding subterranean formation through the casing string. It thus becomes necessary to seal the wellbore and thereby provide zonal isolation at the location of the desired subterranean formation. Wellbore isolation devices, such as packers, bridge plugs, and fracturing plugs (i.e., "frac" plugs), are designed for these general purposes and are well known in the art of producing hydrocarbons, such as oil and gas. Such wellbore isolation devices may be used in direct contact with the formation face of the wellbore, with a casing string extended and secured within the wellbore, or with a screen or wire mesh.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Figure 1:
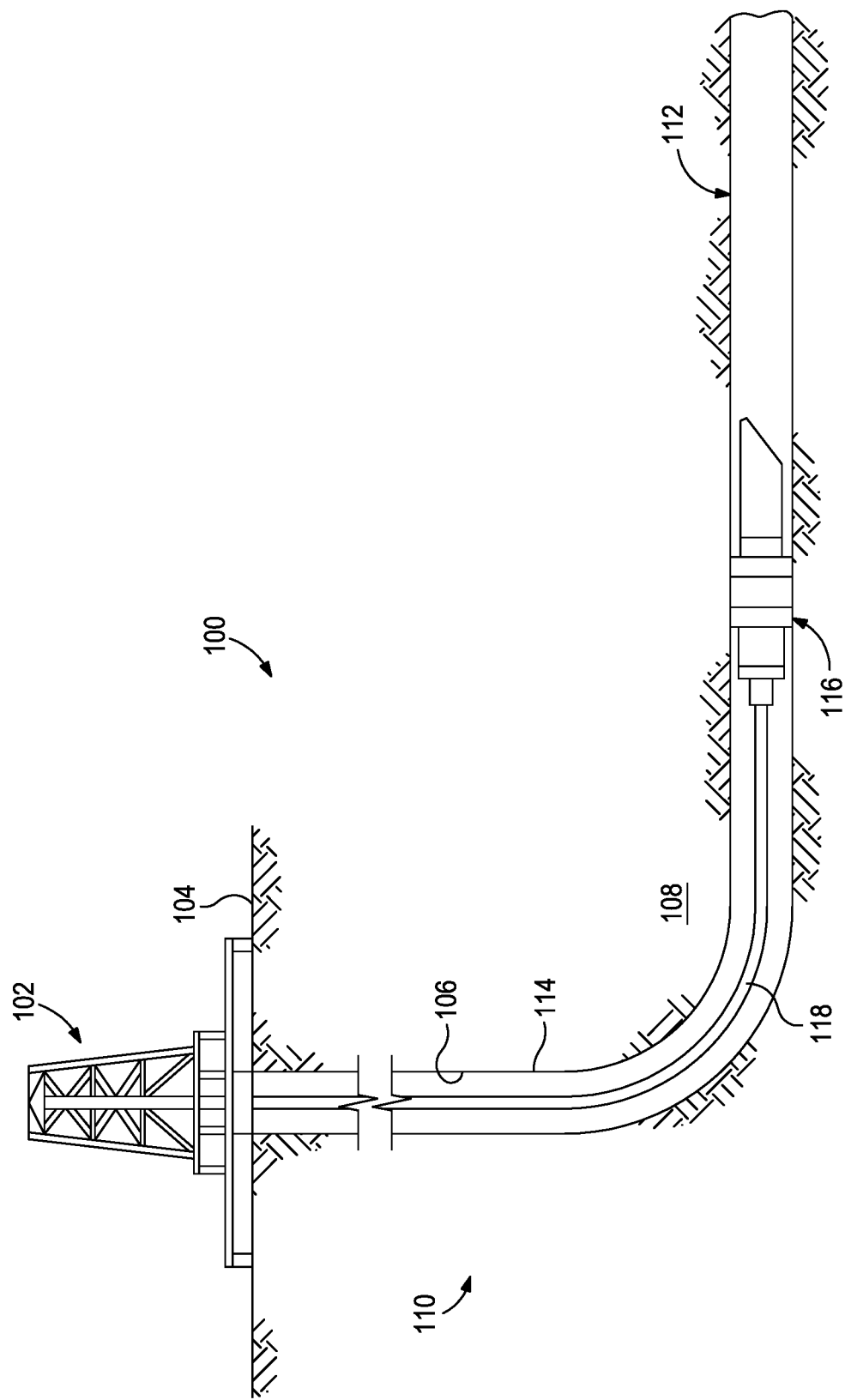
FIG. 1 is a well system that can employ one or more principles of the present disclosure, according to one or more embodiments.

The present disclosure describes embodiments of wellbore isolation devices with components, specifically, wear bands and slips, having modified surfaces to change the frictional properties between the components and the surrounding wellbore surface, which may be a formation face, a casing string, a screen, a wire mesh, or a combination thereof. In particular, the present disclosure describes wear bands with modified surfaces that reduce the friction between the wear band and the surrounding wellbore surface when conveying the wellbore tool through the wellbore. Further, the present disclosure describes slips with modified surface that increase the friction between the slips and the surrounding wellbore surface when the wellbore tool is in the set position. In some instances, the wear bands and slips may be degradable.

As used herein, the term "wellbore isolation device," and grammatical variants thereof, is a device that is set in a wellbore to isolate a portion of the wellbore thereabove from a portion therebelow so that fluid can be forced into the surrounding subterranean formation above the device. As used herein, the term "sealing ball" and "frac ball," and grammatical variants thereof, refer to a spherical or spheroidal element designed to seal a portion of a wellbore isolation device that is accepting fluids like the inner diameter of a mandrel, thereby diverting reservoir treatments to other portions of a target zone in a subterranean formation. An example of a sealing ball is a frac ball in a frac plug wellbore isolation device. As used herein, the term "packer element," and grammatical variants thereof, refers to an expandable, inflatable, or swellable element that expands against a casing or wellbore to seal the wellbore.

One or more illustrative embodiments disclosed herein are presented below. Not all features of an actual implementation are described or shown in this application for the sake of clarity. It is understood that in the development of an actual embodiment incorporating the embodiments disclosed herein, numerous implementation-specific decisions must be made to achieve the developer's goals, such as compliance with system-related, lithology-related, business-related, government-related, and other constraints, which vary by implementation and over time. While a developer's efforts might be complex and time-consuming, such efforts would be, nevertheless, a routine undertaking for those of ordinary skill in the art having benefit of this disclosure.

It should be noted that when "about" is provided herein at the beginning of a numerical list, the term modifies each number of the numerical list. In some numerical listings of ranges, some lower limits listed may be greater than some upper limits listed. One skilled in the art will recognize that the selected subset will require the selection of an upper limit in excess of the selected lower limit. Unless otherwise indicated, all numbers expressing quantities of ingredients, properties such as molecular weight, reaction conditions, and so forth used in the present specification and associated claims are to be understood as being modified in all instances by the term "about." As used herein, the term "about" encompasses +/−5% of each numerical value. For example, if the numerical value is "about 80%," then it can be 80%+/−5%, equivalent to 76% to 84%. Accordingly, unless indicated to the contrary, the numerical parameters set forth in the following specification and attached claims are approximations that may vary depending upon the desired properties sought to be obtained by the exemplary embodiments described herein. At the very least, and not as an attempt to limit the application of the doctrine of equivalents to the scope of the claim, each numerical parameter should at least be construed in light of the number of reported significant digits and by applying ordinary rounding techniques.

While compositions and methods are described herein in terms of "comprising" various components or steps, the compositions and methods can also "consist essentially of" or "consist of" the various components and steps. When "comprising" is used in a claim, it is open-ended.

As used herein, the term "substantially" means largely, but not necessarily wholly.

The use of directional terms such as above, below, upper, lower, upward, downward, left, right, uphole, downhole and the like are used in relation to the illustrative embodiments as they are depicted in the figures, the upward direction being toward the top of the corresponding figure and the downward direction being toward the bottom of the corresponding figure, the uphole direction being toward the surface of the well and the downhole direction being toward the toe of the well.

The embodiments of the present disclosure are directed toward wellbore isolation devices (e.g., frac plugs, bridge plugs, and packers) comprising wear bands with a modified surface and/or and slips with a modified surface, where the wear bands and/or the slips may optionally be degradable. The wear bands of the isolation device are structures that are often coupled to a mule shoe, extend radially beyond most or all surfaces of the isolation device in the unset position, and contact the wellbore surface as the wellbore isolation device is conveyed through the wellbore to a desired location. Then, once in a desired location, the wellbore isolation device is transitioned to a set position where the slips or a component coupled thereto (e.g., buttons coupled thereto) frictionally engage the wellbore surface and a packer element is compressed against the wellbore surface. As used herein, the term "unset position" refers to a configuration of a wellbore isolation tool where the packer element is not compressively engaged with the wellbore surface. As used herein, the term "set position" refers to a configuration of a wellbore isolation tool where the packer element is compressively engaged with the wellbore surface.

Once set the wellbore isolation device fluidly separates or fluidly isolates two portions of the wellbore. In some instances, the fluid isolation may reduce or eliminate fluid flow between both portions. Alternatively, the fluid isolation may reduce or eliminate fluid flow from one portion to the other while still allowing fluid flow in the opposite direction. After fluidly isolating two portions of the wellbore, a wellbore operation may be performed on one or both portions of the wellbore. For example, the subterranean formation may be hydraulically fractured through the at least one perforation formed in an isolated portion of the wellbore. As used herein, the term "hydraulic fracturing," and grammatical variants thereof, refers to a stimulation treatment in which fluids are pumped at a high rate and pressure to overcome a fracture gradient within a subterranean formation to cause fractures to be created or enhanced. The term "fracture gradient," and grammatical variants thereof, refers to the pressure required to induce or enhance fractures in a subterranean formation at a given depth. That is, the fracture gradient may vary in a particular subterranean formation depending on the depth thereof.

During the hydraulic fracturing operation, at least one perforation is created in the subterranean formation though wellbore surface (e.g., the formation face of the wellbore or the casing string and any cement disposed between the formation face and the casing string, if included). In some embodiments, a plurality of perforations, or a perforation cluster are created into the subterranean formation, without departing from the scope of the present disclosure. As used herein, the term "perforation," and grammatical variants thereof, refers to a communication tunnel created through a wall of a wellbore, including through a casing string, into a subterranean formation through which production fluids may flow. Perforations may be formed by any means suitable in a subterranean formation including, but not limited to, shaped explosive charges, perforating guns, bullet perforating, abrasive jetting, or high-pressure fluid jetting, without departing from the scope of the present disclosure.

FIG. 1 illustrates a well system 100 that may embody or otherwise employ one or more principles of the present disclosure, according to one or more embodiments. As illustrated, the well system 100 may include a service rig 102 (also referred to as a "derrick") that is positioned on the earth's surface 104 and extends over and around a wellbore 106 that penetrates a subterranean formation 108. The service rig 102 may be a drilling rig, a completion rig, a workover rig, or the like. In some embodiments, the service rig 102 may be omitted and replaced with a standard surface wellhead completion or installation, without departing from the scope of the disclosure. While the well system 100 is depicted as a land-based operation, it will be appreciated that the principles of the present disclosure could equally be applied in any sea-based or sub-sea application where the service rig 102 may be a floating platform or sub-surface wellhead installation, as generally known in the art.

The wellbore 106 may be drilled into the subterranean formation 108 using any suitable drilling technique and may extend in a substantially vertical direction away from the earth's surface 104 over a vertical wellbore portion 110. At some point in the wellbore 106, the vertical wellbore portion 110 may deviate from vertical relative to the earth's surface 104 and transition into a substantially horizontal wellbore portion 112, although such deviation is not required. That is, the wellbore 106 may be vertical, horizontal, or deviated, without departing from the scope of the present disclosure. In some embodiments, the wellbore 106 may be completed by cementing a string of casing 114 within the wellbore 106 along all or a portion thereof. As used herein, the term "casing" refers not only to casing as generally known in the art, but also to borehole liner, which comprises tubular sections coupled end to end but not extending to a surface location. In other embodiments, however, the string of casing 114 may be omitted from all or a portion of the wellbore 106 and the principles of the present disclosure may equally apply to an "open-hole" environment.

The well system 100 may further include a wellbore isolation device 116 that may be conveyed into the wellbore 106 on a conveyance 118 (also referred to as a "tool string") that extends from the service rig 102. The wellbore isolation device 116 may include or otherwise comprise any type of casing or borehole isolation device known to those skilled in the art including, but not limited to, a frac plug, a bridge plug, a deployable baffle, a wellbore packer, a wiper plug, a cement plug, or any combination thereof.

The conveyance 118 that delivers the wellbore isolation device 116 downhole may be, but is not limited to, wireline, slickline, an electric line, coiled tubing, drill pipe, production tubing, or the like. The wellbore isolation device 116 may be conveyed downhole to a target location (not shown) within the wellbore 106. At the target location, the wellbore isolation device may be actuated or "set" to seal the wellbore 106 and otherwise provide a point of fluid isolation within the wellbore 106. In some embodiments, the wellbore isolation device 116 is pumped to the target location using hydraulic pressure applied from the service rig 102 at the surface 104. In such embodiments, the conveyance 118 serves to maintain control of the wellbore isolation device 116 as it traverses the wellbore 106 and provides the necessary power to actuate and set the wellbore isolation device 116 upon reaching the target location. In other embodiments, the wellbore isolation device 116 freely falls to the target location under the force of gravity to traverse all or part of the wellbore 106.

It will be appreciated by those skilled in the art that even though FIG. 1 depicts the wellbore isolation device 116 as being arranged and operating in the horizontal portion 112 of the wellbore 106, the embodiments described herein are equally applicable for use in portions of the wellbore 106 that are vertical, deviated, or otherwise slanted. It should also be noted that a plurality of wellbore isolation devices 116 may be placed in the wellbore 106. In some embodiments, for example, several (e.g., six or more) wellbore isolation devices 116 may be arranged in the wellbore 106 to divide the wellbore 106 into smaller intervals or "zones" for hydraulic stimulation.

Figure 2:
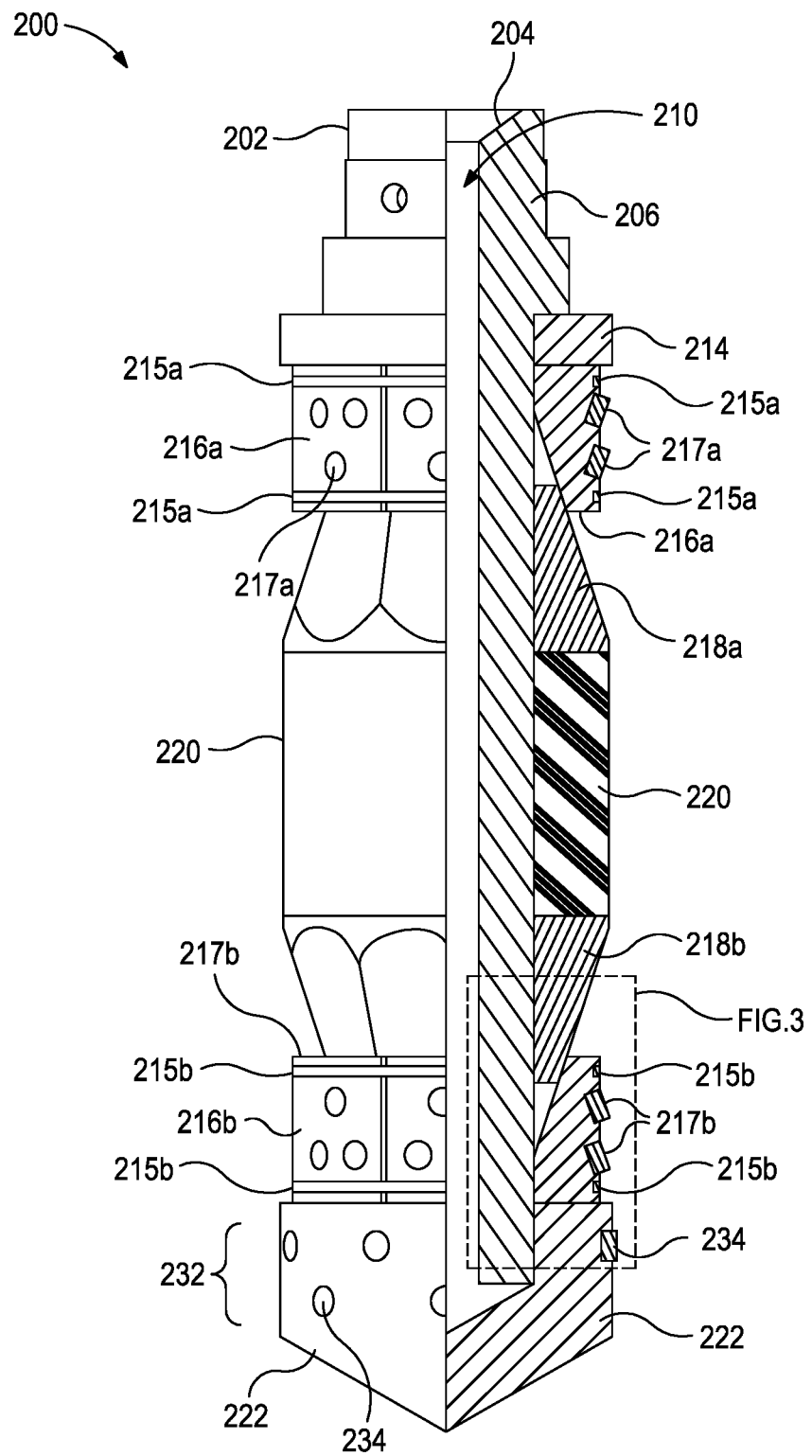
FIG. 2 is a cross-sectional side view of a frac plug that can employ the principles of the present disclosure.

FIG. 2, with continued reference to FIG. 1, illustrates a side view of an exemplary frac plug 200 that may employ one or more principles of the present disclosure. As used herein, the term "frac plug" (also referred to as a "fracturing plug"), and grammatical variants thereof, refers to a wellbore isolation device that isolates fluid flow in at least one direction relative to the plug, typically the isolation is from above the plug. While the present disclosure uses frac plugs to illustrate various embodiments of wear bands and/or slips having modified surfaces, these embodiments may be applied to the wear bands and/or slips of the other foregoing wellbore isolation devices and are within the scope of the present application.

The frac plug 200 in an unset position 202 may be similar to or the same as the wellbore isolation device 116 of FIG. 1. Accordingly, the frac plug 200 may be configured to be extended into and seal the wellbore 106 at a target location, and thereby prevent fluid flow past the frac plug 200 for wellbore completion or stimulation operations. In some embodiments, as illustrated, the wellbore 106 may be lined with the casing 114 or another type of wellbore liner or tubing in which the frac plug 200 may suitably be set. In other embodiments, however, the casing 114 may be omitted and the frac plug 200 may instead be set or otherwise deployed in an uncompleted or "open-hole" environment.

A mandrel 206 defines a longitudinal central flow passage 210. The mandrel 206 also defines a ball seat 204 at its upper end. In some embodiments, the frac ball 208 may be dropped into the conveyance 118 (FIG. 1) to land on top of the frac plug 200 at the ball seat 204 so as to actuate the frac plug from an unset position 202 to a set position.

One or more spacer rings 214 (one shown) may be secured to the mandrel 206 and otherwise extend thereabout. The spacer ring 214 provides an abutment, which axially retains a set of upper slips 216a that are also positioned circumferentially about the mandrel 206. As illustrated, a set of lower slips 216b may be arranged distally from the upper slips 216a. The upper slips 216a constrain the upper slip bands 215a; and the lower slips 216b are constrained by the lower slip bands 215b. As used herein, the term "constrained" means at least partially enclosed within a supporting substance material. The slip bands 215a,215b may constrain the slips 216a,216b, respectively, by any known method. Examples of suitable methods may include, but are not limited to, via a press fit, via a thermal shrink fit, via an adhesive, interference fit, clearance fit, via a snap ring, and the like.

The slips 216a,216b have buttons 217a,217b embedded therein. The buttons 217a,217b protrude from the slips 216a,216b, respectively, to frictionally engage a wellbore surface (e.g., a wellbore wall, a tubing string wall, such as casing string, and the like) when the frac plug 200 is actuated from the unset position 202 to the set position. In preferred embodiments, the buttons 217a,217b penetrate or bite into the downhole surface. Although each slip 216a,216b is shown having two slip bands 215a,215b and three or four buttons 217a,217b coupled thereto, respectfully, it will be appreciated that any number of slip bands and buttons, including one or a plurality (two, three, four, five, six, eight, ten, twenty, and the like) of slip bands and/or one or a plurality (two, three, four, five, six, eight, ten, twenty, and the like) buttons may be coupled to each slip, without departing from the scope of the present disclosure. Moreover, the number of slip bands in the upper slips 216a and lower slips 216b, and any additional slips included as part of the frac plug 200, may have the same or different number of slip bands, without departing from the scope of the present disclosure. Additionally, although the slip bands 215a,215b shown in FIG. 2 are depicted as rectangular or square in cross section, the slip bands 215a,215b may be any other shape, without departing from the scope of the present disclosure. For example, the shape of the slips bands may be cylindrically shaped, frustrum shaped, conical shaped, spheroid shaped, pyramid shaped, polyhedron shaped, octahedron shaped, cube shaped, prism shaped, hemispheroid shaped, cone shaped, tetrahedron shaped, cuboid shaped, and the like, and any combination thereof, without departing from the scope of the present disclosure. That is, the slip bands may be partially one shape and partially one or more other shapes.

One or more slip wedges 218 (shown as upper and lower slip wedges 218a and 218b, respectively) may also be positioned circumferentially about the mandrel 206, as described in greater detail below. Collectively, the term "slip assembly" includes at least the slips 216a,216b, the slip bands 215a,215b, the buttons 217a,217b, and slip wedges 218a,218b.

A packer assembly comprising one or more expandable or inflatable packer elements 220 (also referred to herein collectively as packer element 220) may be disposed between the upper slip wedges 218a,318a, and lower slip wedges 218b and otherwise arranged about the mandrel 206. It will be appreciated that the particular packer assembly depicted in FIG. 2 is merely representative as there are several packer arrangements known and used within the art. For instance, while three packer elements 220 are shown in FIG. 2, the principles of the present disclosure are equally applicable to wellbore isolation devices that employ more or less than three packer elements 220, without departing from the scope of the disclosure.

A mule shoe 222 may be positioned at or otherwise secured to the mandrel 206 at its lower or distal end. As will be appreciated, the lowermost portion of the frac plug 200 need not be mule shoe 222, but could be any type of section that serves to terminate the structure of the frac plug 200, or otherwise serves as a connector for connecting the frac plug 200 to other tools, such as a valve, tubing, or other downhole equipment. The mule shoe 222 includes a wear band 232 coupled thereto and extending therefrom, which is illustrated as a plurality of buttons 234 coupled to the mule shoe 222 arranged about the mule shoe 222. In alternative embodiments, a wear band may be a structure that encircles the mule shoe 222.

As the frac plug 200 moves radially off-center within the wellbore during placement of the frac plug 200, the surface of the wear band 232 contacts the wellbore surface. The wear band 232 preferably provide a surface with reduced friction that allows the frac plug 200 to pass more easily through the wellbore. The wear band 232 preferably provides a surface with greater abrasion resistance that allows the frac plug 200 to, preferably, pass without losing diameter through the wellbore.

Once the frac plug 200 reaches the target location, a setting tool (not shown) of a type known in the art can be used to move the frac plug 200 from the unset position 202 to the set position. The setting tool may operate via various mechanisms to anchor the frac plug 200 in the wellbore 106 including, but not limited to, hydraulic setting, mechanical setting, setting by swelling, setting by inflation, and the like.

After actuating the frac plug 200, the slip bands 215a, 215b rupture or are otherwise compromised to allow (1)

expansion of the packer elements 220 and compression against the wellbore 106 and (2) the slips 216a,216b to frictionally engage the wellbore 106. For example, the frangible barrier may be broken by stroking of the mandrel 206, mere shear contact with the wellbore 106 or other portions of the wellbore 106, or by other mechanical means, thus exposing the packer elements 220 to the wellbore environment. Thereafter, the packer elements 220 may themselves be swellable or the rupture of the frangible barrier may trigger a mechanical actuation of the frac plug 200 to cause the packer elements 220 to expand and compress against the wellbore 106. Other means of compressing the packer elements 220 against the wellbore 106 may additionally be appropriate in accordance with the embodiments described herein, without departing from the scope of the present disclosure.

After the frac plug 200 is set, completion or stimulation operations may be undertaken by injecting a treatment or completion fluid into the wellbore 106 and forcing the treatment/completion fluid out of the wellbore 106 and into a subterranean formation above the frac plug 200. Following completion and/or stimulation operations, the frac plug 200 must be removed from the wellbore 106 in order to allow production operations to effectively occur without being excessively hindered by the emplacement of the frac plug 200.

Figure 3:
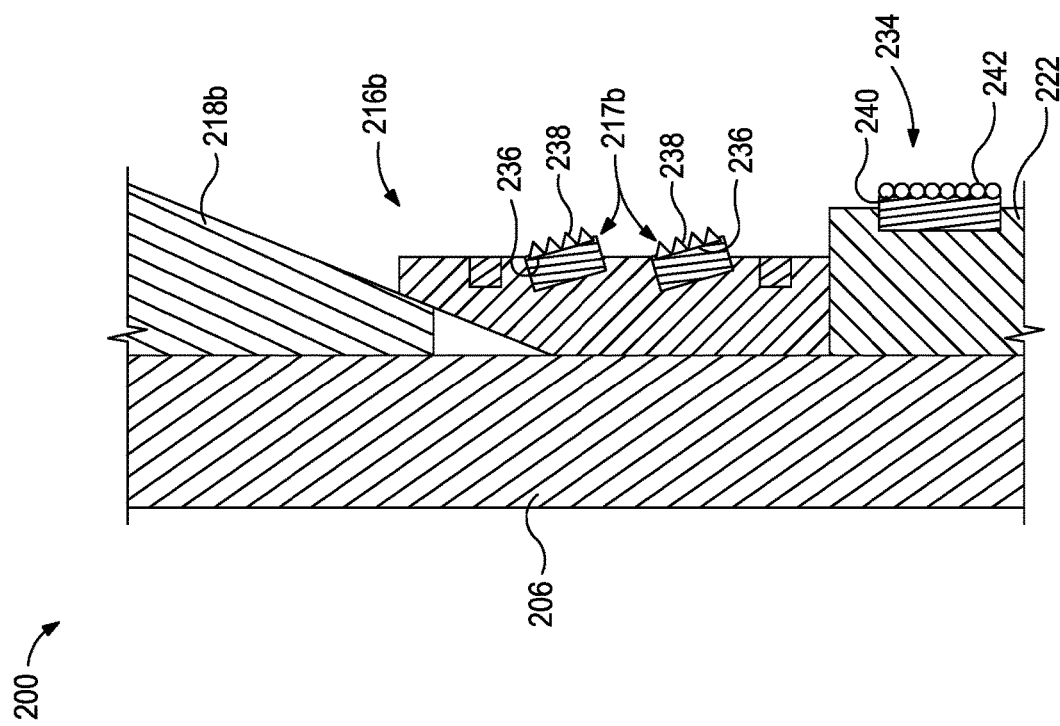
FIG. 3 is an expanded view of a portion of the frac plug of FIG. 2 illustrating the modified surfaces of the buttons of the slip and the wear band.

FIG. 3 is an expanded view of a portion of the frac plug 200 illustrating the modified surface 236 of the buttons 217b of the slip 216b and the modified surface 236,240 of the button 234 of the wear band, respectively.

The buttons 217b of the slip 216b include a modified surface 236 formed by particles 238 coupled to the button 217b. The particles 238 preferably include at least some sharp protrusions (i.e., protrusions with the smallest angle at the point being about 120° or less and, preferably, 90° or less). The shape of the particles 238 may be spherical with sharp protrusion, ovular with sharp protrusions, cube, triangular, conical, irregular, and the like. While the particles 238 may be larger, the particles 238 may have an average diameter of about 0.75 cm or less (e.g., about 0.1 cm to about 0.75 cm, about 0.1 cm to about 0.5 cm, about 0.1 cm to about 0.25 cm, about 0.25 cm to about 0.75 cm, or about 0.25 cm to about 0.5 cm). As used herein, "diameter" of particles refers to the largest cross-sectional distance of the particles.

In some instances, the button 217b may be ceramic, and the particles 238 may be coupled thereto with an adhesive (e.g., epoxy). In some instances, the button 217b may be polymeric, and the particles 238 may be coupled thereto with an adhesive or by sintering to partially embed the particles 238 into the polymer. In some instances, the button 217b may be metallic, and the particles 238 may be coupled thereto with an adhesive, by brazing, or by heating and pressing the particles 238 into the metal to partially embed the particles 238 into the metal.

In alternative embodiments, the buttons 217b of the slip 216b may be machined or roughened to have a surface with sharp protrusions.

In FIGS. 2-3, the modified surface 236 of the buttons 217b of the slip 216b as being at an angle relative to the wellbore surface, which may allow for the button 217b to bite into the wellbore surface on a macroscale while the modified surface 236 bites into the wellbore surface on a microscale. In alternative embodiments, the buttons on the slips may be configured such that the modified surface parallel to the wellbore surface and relies primarily on the modified surface to bite into the wellbore surface.

The button 234 of the wear band 232 includes a modified surface 240 formed by particles 242 coupled to the button 234. The particles 242 preferably include smooth surfaces substantially absent of sharp protrusions facing outward toward the casing when in use. That is, the particles 242 should be shaped so as not to brinnel or bite into the casing but rather produce with minimal friction with the casing wall when conveying the frac plug 200 or other tool. In some instances, the surface of the particles 242 facing or potentially contacting the casing may preferably be rounded or have angles larger than 120° to mitigate biting into the casing. For example, the shape of the particles 242 may be spherical, ovular, prolate, polyhedron, and the like. While the particles 242 may be larger, the particles 242 may have an average diameter of about 0.75 cm or less (e.g., about 0.1 cm to about 0.75 cm, about 0.1 cm to about 0.5 cm, about 0.1 cm to about 0.25 cm, about 0.25 cm to about 0.75 cm, or about 0.25 cm to about 0.5 cm).

In some instances, the button 234 of the wear band 232 may be ceramic, and the particles 242 may be coupled thereto with an adhesive. In some instances, the button 234 of the wear band 232 may be polymeric, and the particles 242 may be coupled thereto with an adhesive or by sintering to partially embed the particles 242 into the polymer. In some instances, the button 234 of the wear band 232 may be metallic, and the particles 242 may be coupled thereto with an adhesive, by brazing, or by heating and pressing the particles 242 into the metal to partially embed the particles 242 into the metal. The particles 242 may be located towards the surface of the button 234, as shown in FIG. 3, or the particles may be distributed throughout the body of the button 234. In the preferred embodiment, the particles 242 are distributed throughout the body of the button 234.

Because the buttons 217b,234 have a size that is sufficiently large to be considered unwanted debris within the wellbore, in some embodiments, the buttons 217b of the slip 216b and/or the button 234 of the wear band may be composed of a degradable material, examples of which are provided further herein. However, the mechanical properties for some degradable materials may be lesser than the mechanical properties for non-degradable materials. As such, the particles 238,242 may be chosen to provide a surface with desired mechanical properties. The particles 238,242 may be surface treated, such as with siloxane, in order to increase the bond strength with the degradable material and, thus, for the particles 238,242 to act as a strengthening or reinforcement material in the buttons 217b, 234. In another example, the degradable material of the buttons 217b may have compressive strength slightly below the desired compressive stress of such button or wear band. Accordingly, the particles 238 may be composed of a material that has higher friction and will lock together. For example, a tungsten carbide button may comprise a binder of cobalt or nickel and tungsten carbide particles. The tungsten carbide particles may be sizes and/or shaped to provide for the properties desired, and the binder content may be reduced toward a minimum amount to increase the compressive strength of the total button.

Because the particles 238,242 are sufficiently small to traverse the wellbore and other tools within or couple thereto without causing issue, the particles 238,242 may be composed of degradable or non-degradable materials. Exemplary materials that the particles 238,242 may be composed of may include, but are not limited to, iron, steel, aluminum alloys, iron alloys, silica, silicate (a mixed oxide of silicon), titania, alumina, aluminate (a mixed oxide of aluminum), aluminosilicate, bauxite, sand, garnet, glass, carbon composites, carbides, nitrides, and the like, and any combination thereof.

Figure 4:
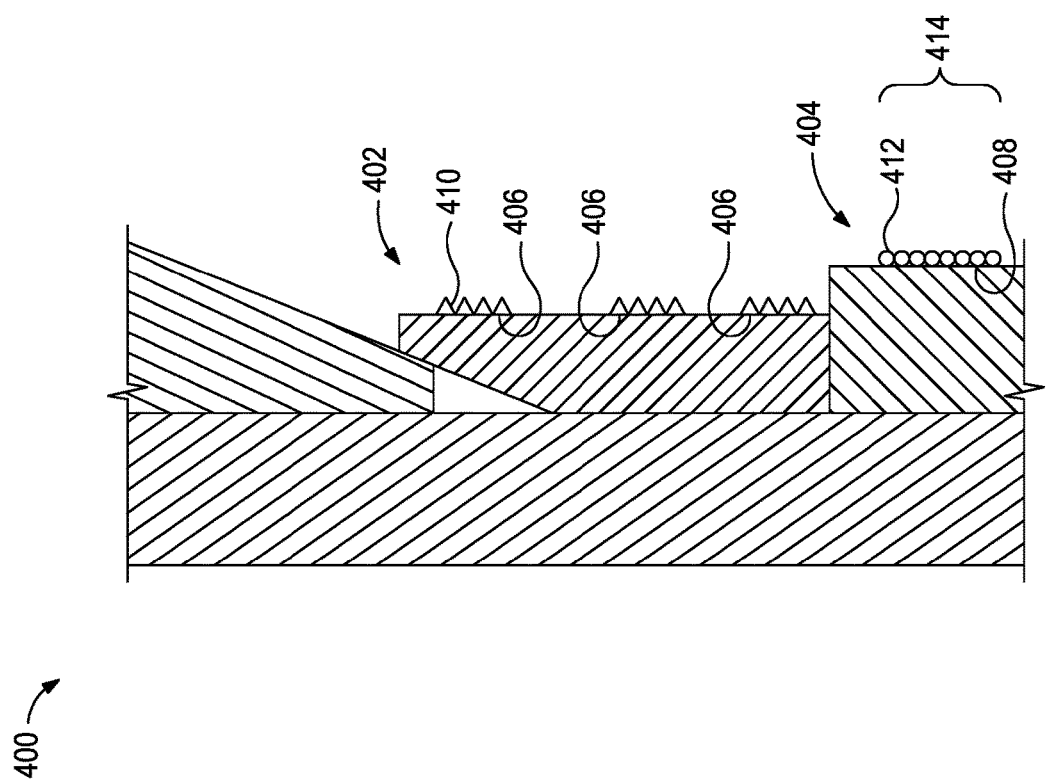
FIG. 4 is an expanded view of a portion of an alternative frac plug illustrating modified surfaces of a slip and a mule shoe.

FIG. 4 is an expanded view of a portion of an alternative frac plug 400 illustrating modified surfaces 406,408 of a slip 402 and a mule shoe 404, respectively. In this example, the particles 410,412 are coupled directly to the slip 402 and the mule shoe 404 rather than buttons or other structure coupled to the slip 402 and mule shoe 404 as illustrated in FIGS. 2-3. The particles 410 preferably include at least some sharp protrusions and are coupled to the slip 402 (e.g., as described relative to particles 238 and button 217b in FIG. 3) to form the modified surface 406. The modified surface 406 may be the entire surface of the slip 402 that engages the wellbore surface or a portion thereof.

The particles 412 preferably have smooth surfaces substantially absent of sharp protrusions and are coupled to the mule shoe 404 (e.g., as described relative to particles 242 and button 234 in FIG. 3) to form the modified surface 408 that defines the wear band 414. The wear band 414 may be the entire surface of the mule shoe 404 that engages the wellbore surface or a portion thereof. As illustrated, the wear band 414 is only a portion of the mule shoe 404.

In some instances, the slips, the mule shoes, the buttons, the mandrel, the packer element, other components of a wellbore isolation device, or a combination thereof may be at least partially degradable. As used herein, the term "degradable" and all of its grammatical variants (e.g., "degrade," "degradation," "degrading," "dissolve," dissolving," and the like), refers to the dissolution or chemical conversion of solid materials such that reduced-mass solid end products result or reduced structural integrity results by at least one of solubilization, hydrolytic degradation, biologically formed entities (e.g., bacteria or enzymes), chemical reactions (including electrochemical and galvanic reactions), thermal reactions, reactions induced by radiation, or combinations thereof. In complete degradation, no solid end products result, or structural shape is lost. In some instances, the degradation of the material may be sufficient for the mechanical properties of the material to be reduced to a point that the material no longer maintains its integrity and, in essence, falls apart or sloughs off into its surroundings. The conditions for degradation are generally wellbore conditions where an external stimulus may be used to initiate or effect the rate of degradation, where the external stimulus is naturally occurring in the wellbore (e.g., pressure, temperature) or introduced into the wellbore (e.g., fluids, chemicals). For example, the pH of the fluid that interacts with the material may be changed by introduction of an acid or a base, or an electrolyte may be introduced or naturally occurring to induce galvanic corrosion. The term "wellbore environment," and grammatical variants thereof, includes both naturally occurring wellbore environments and materials or fluids introduced into the wellbore. The term "at least a portion," and grammatical variants thereof, with reference to a component having at least a portion composed thereof of a degradable material or substance (e.g., "at least a portion of a component is degradable" or "at least a portion of the button is degradable," and variants thereof) refers to at least about 80% of the volume of that part being formed of the degradable material or substance.

The degradable materials of the degradable components may allow for time between setting the wellbore isolation device and when a particular downhole operation is undertaken, such as a hydraulic fracturing operation). Moreover, degradable materials allow for acid treatments and acidified stimulation of a wellbore. In some embodiments, the degradable materials may require a greater flow area or flow capacity to enable production operations without unreasonably impeding or obstructing fluid flow while the wellbore isolation device degrades. As a result, production operations may be efficiently undertaken while the wellbore isolation device degrades and without creating significant pressure restrictions.

Exemplary degradable materials include, but are not limited to, degradable polymer and degradable metals that may be degradable by exposure to hydrocarbon fluids, acidic fluid, electrolyte fluids, or a combination thereof. Referring now to the degradable metal materials of the present disclosure, the term "degradable metal material" (also referred to simply as "degradable metal" herein) may refer to the rate of dissolution of the degradable metal material, and the rate of dissolution may correspond to a rate of material loss at a particular temperature and within a particular wellbore environment, such as in the presence of an electrolyte. In at least one embodiment, the degradable metal materials described herein exhibit an average degradation rate in an amount of greater than about 0.01 milligrams per square centimeters (mg/cm$^2$) per hour at 93° C. (equivalent to about 200° F.) while exposed to a 15% potassium chloride (KCl) solution. For example, in some embodiments, the degradable metal materials may have an average degradation rate of greater than in the range of from about 0.01 mg/cm$^2$ to about 10 mg/cm$^2$ per hour at a temperature of about 93° C. while exposed to a 15% KCl solution, encompassing any value and subset therebetween. For example, the degradation rate may be about 0.01 mg/cm$^2$ to about 2.5 mg/cm$^2$, or about 2.5 mg/cm$^2$ to about 5 mg/cm$^2$, or about 5 mg/cm$^2$ to about 7.5 mg/cm$^2$, or about 7.5 mg/cm$^2$ to about 10 mg/cm$^2$ per hour at a temperature of 93° C. while exposed to a 15% KCl solution, encompassing any value and subset therebetween.

In other instances, the degradable metal material may exhibit a degradation rate such that it loses greater than about 0.1% of its total mass per day at 93° C. in a 15% KCl solution. For example, in some embodiments, the degradable metal materials described herein may have a degradation rate such that it loses about 0.1% to about 10% of its total mass per day at 93° C. in a 15% KCl solution, encompassing any value and subset therebetween. For example, in some embodiments the degradable metal material may lose about 0.1% to about 2.5%, or about 2.5% to about 5%, or about 5% to about 7.5%, or about 7.5% to about 10% of its total mass per day at 93° C. in a 15% KCl solution, encompassing any value and subset therebetween. Each of these values representing the degradable metal material is critical to the embodiments of the present disclosure and may depend on a number of factors including, but not limited to, the type of degradable metal material, the wellbore environment, and the like.

It should be noted that the various degradation rates noted in a 15% KCl solution are merely a means of defining the degradation rate of the degradable metal materials described herein by reference to contact with a specific electrolyte at a specific temperature. The use of the wellbore isolation device having a degradable metal material may be exposed to other wellbore environments to initiate degradation, without departing from the scope of the present disclosure.

It should be further noted, that the non-metal degradable materials also discussed herein, which may be used for forming components of the wellbore isolation device may additionally have a degradation rate in the same amount or range as that of the degradable metal material, which may allow use of certain degradable materials that degrade at a rate faster or slower than other degradable materials (including the degradable metal materials) for forming the wellbore isolation device.

The degradation of the degradable metal material may be in the range of from about 5 days to about 40 days, encompassing any value or subset therebetween. For example, the degradation may be about 5 days to about 10 days, or about 10 days to about 20 days, or about 20 days to about 30 days, or about 30 days to about 40 days, encompassing any value and subset therebetween. Each of these values representing the degradable metal material is critical to the embodiments of the present disclosure and may depend on a number of factors including, but not limited to, the type of degradable metal material, the wellbore environment, and the like.

Suitable degradable metal materials that may be used in accordance with the embodiments of the present disclosure include galvanically-corrodible or degradable metals and metal alloys. Such metals and metal alloys may be configured to degrade via galvanic corrosion in the presence of an electrolyte (e.g., brine or other salt-containing fluids present within the wellbore 106). As used herein, an "electrolyte" is any substance containing free ions (i.e., a positively or negatively charged atom or group of atoms) that make the substance electrically conductive. The electrolyte can be selected from the group consisting of solutions of an acid, a base, a salt, and combinations thereof.

Electrolytes may include, but are not limited to, a halide anion (i.e., fluoride, chloride, bromide, iodide, and astatide), a halide salt, an oxoanion (including monomeric oxoanions and polyoxoanions), and any combination thereof. Suitable examples of halide salts for use as the electrolytes of the present disclosure may include, but are not limited to, a potassium fluoride, a potassium chloride, a potassium bromide, a potassium iodide, a sodium chloride, a sodium bromide, a sodium iodide, a sodium fluoride, a calcium fluoride, a calcium chloride, a calcium bromide, a calcium iodide, a zinc fluoride, a zinc chloride, a zinc bromide, a zinc iodide, an ammonium fluoride, an ammonium chloride, an ammonium bromide, an ammonium iodide, a magnesium chloride, potassium carbonate, potassium nitrate, sodium nitrate, and any combination thereof. The oxyanions for use as the electrolyte of the present disclosure may be generally represented by the formula $A_xO_y^{z-}$, where A represents a chemical element and O is an oxygen atom; x, y, and z are integers between the range of about 1 to about 30, and may be or may not be the same integer. Examples of suitable oxoanions may include, but are not limited to, carbonate (e.g., hydrogen carbonate ($HCO_3^-$)), borate, nitrate, phosphate (e.g., hydrogen phosphate ($HPO_4^{2-}$)), sulfate, nitrite, chlorite, hypochlorite, phosphite, sulfite, hypophosphite, hyposulfite, triphosphate, and any combination thereof. Other common free ions that may be present in an electrolyte may include, but are not limited to, sodium ($Na^+$), potassium ($K^+$), calcium ($Ca^{2+}$), magnesium ($Mg^{2+}$), and any combination thereof. Preferably, the electrolyte contains chloride ions. The electrolyte can be a fluid that is introduced into the wellbore 106 or a fluid emanating from the wellbore 106, such as from a surrounding subterranean formation (e.g., the formation 108 of FIG. 1).

In some embodiments, the electrolyte may be present in an aqueous base fluid up to saturation for contacting the degradable metal material components of the wellbore isolation device, which may vary depending on the type of degradable metal material, the aqueous base fluid selected, and the like, and any combination thereof. In other embodiments, the electrolyte may be present in the aqueous base fluid in the range of from about 0.001% to about 30% by weight of the aqueous base fluid, encompassing any value and subset therebetween. For example, the electrolyte may be present of from about 0.001% to about 0.01%, or about 0.01% to about 1%, or about 1% to about 6%, or about 6% to about 12%, or about 12% to about 18%, or about 18% to about 24%, or about 24% to about 30% by weight of the aqueous base fluid. Each of these values is critical to the embodiments of the present disclosure and may depend on a number of factors including, but not limited to, the composition of the degradable metal material, the components of the wellbore isolation device composed of the degradable metal material, the type of electrolyte selected, other conditions of the wellbore environment, and the like.

The degradable metal materials for use in forming at least buttons of the slips, the wear band, the buttons of the wear band, the slips, or other components of the wellbore isolation tool for use in implementing the methods described herein may include a metal material that is galvanically corrodible in a wellbore environment, such as in the presence of an electrolyte, as previously discussed. Suitable such degradable metal materials may include, but are not limited to, gold, gold-platinum alloys, silver, nickel, nickel-copper alloys, nickel-chromium alloys, copper, copper alloys (e.g., brass, bronze, etc.), chromium, tin, tin alloys (e.g., pewter, solder, etc.), aluminum, aluminum alloys (e.g., silumin alloy, a magnalium alloy, etc.), iron, iron alloys (e.g., cast iron, pig iron, etc.), zinc, zinc alloys (e.g., zamak, etc.), magnesium, magnesium alloys (e.g., elektron, magnox, etc.), beryllium, beryllium alloys (e.g., beryllium-copper alloys, beryllium-nickel alloys), and any combination thereof.

Suitable magnesium alloys include alloys having magnesium at a concentration in the range of from about 60% to about 99.95% by weight of the magnesium alloy, encompassing any value and subset therebetween. In some embodiments, the magnesium concentration may be in the range of about 60% to about 99.95%, 70% to about 98%, and preferably about 80% to about 95% by weight of the magnesium alloy, encompassing any value and subset therebetween. Each of these values is critical to the embodiments of the present disclosure and may depend on a number of factors including, but not limited to, the type of magnesium alloy, the desired degradability of the magnesium alloy, and the like.

Magnesium alloys comprise at least one other ingredient besides the magnesium. The other ingredients can be selected from one or more metals, one or more non-metals, or a combination thereof. Suitable metals that may be alloyed with magnesium include, but are not limited to, lithium, sodium, potassium, rubidium, cesium, beryllium, calcium, strontium, barium, aluminum, gallium, indium, tin, thallium, lead, bismuth, scandium, titanium, vanadium, chromium, manganese, iron, cobalt, nickel, copper, zinc, yttrium, zirconium, niobium, molybdenum, ruthenium, rhodium, palladium, praseodymium, silver, lanthanum, hafnium, tantalum, tungsten, terbium, rhenium, osmium, iridium, platinum, gold, neodymium, gadolinium, erbium, oxides of any of the foregoing, and any combinations thereof.

Suitable non-metals that may be alloyed with magnesium include, but are not limited to, graphite, carbon, silicon, boron nitride, and combinations thereof. The carbon can be in the form of carbon particles, fibers, nanotubes, fullerenes, and any combination thereof. The graphite can be in the form of particles, fibers, graphene, and any combination thereof. The magnesium and its alloyed ingredient(s) may be in a solid solution and not in a partial solution or a compound where inter-granular inclusions may be present. In some embodiments, the magnesium and its alloyed ingredient(s) may be uniformly distributed throughout the magnesium alloy but, as will be appreciated, some minor variations in the distribution of particles of the magnesium and its alloyed ingredient(s) can occur. In other embodiments, the magnesium alloy is a sintered construction.

In some embodiments, the magnesium alloy may have a yield stress in the range of from about 15000 pounds per square inch (psi) to about 50000 psi, encompassing any value and subset therebetween. For example, in some embodiments, the magnesium alloy may have a yield stress of about 15000 psi to about 30000 psi, or about 30000 psi to about 40000 psi, or about 40000 psi to about 50000 psi, encompassing any value and subset therebetween. Each of these values is critical to the embodiments of the present disclosure and may depend on a number of factors including, but not limited to, the component of the wellbore isolation device formed from the degradable magnesium alloy, the composition of the degradable magnesium alloy selected, and the like, and any combination thereof.

Suitable aluminum alloys include alloys having aluminum at a concentration in the range of from about 40% to about 99% by weight of the aluminum alloy, encompassing any value and subset therebetween. For example, suitable magnesium alloys may have aluminum concentrations of about 40% to about 50%, or about 50% to about 60%, or about 60% to about 70%, or about 70% to about 80%, or about 80% to about 90%, or about 90% to about 99% by weight of the aluminum alloy, encompassing any value and subset therebetween. Each of these values is critical to the embodiments of the present disclosure and may depend on a number of factors including, but not limited to, the type of aluminum alloy, the desired degradability of the aluminum alloy, and the like.

The aluminum alloys may be wrought or cast aluminum alloys and comprise at least one other ingredient besides the aluminum. The other ingredients can be selected from one or more any of the metals, non-metals, and combinations thereof described above with reference to magnesium alloys, with the addition of the aluminum alloys additionally being able to comprise magnesium.

In some embodiments, the degradable metal materials may be a degradable metal alloy, which may exhibit a nano-structured matrix form and/or inter-granular inclusions (e.g., a magnesium alloy with iron-coated inclusions). Such degradable metal alloys may further include a dopant, where the presence of the dopant and/or the inter-granular inclusions increases the degradation rate of the degradable metal alloy. Other degradable metal materials include solution-structured galvanic material. An example of a solution-structured galvanic material is zirconium (Zr) containing a magnesium (Mg) alloy, where different domains within the alloy contain different percentages of Zr. This leads to a galvanic coupling between these different domains, which cause micro-galvanic corrosion and degradation. Another example of a solution-structured galvanically-corrodible material is a ZK60 magnesium alloy, which includes 4.5% to 6.5% zinc, minimum 0.25% zirconium, 0% to 1% other, and balance magnesium; AZ80, which includes 7.5% to 9.5% aluminum, 0.2% to 0.8% zinc, 0.12% manganese, 0.015% other, and balance magnesium; and AZ31, which includes 2.5% to 3.5% aluminum, 0.5% to 1.5% zinc, 0.2% manganese, 0.15% other, and the balance magnesium. Each of these examples is % by weight of the metal alloy. In some embodiments, "other" may include unknown materials, impurities, additives, and any combination thereof.

The degradable metal magnesium alloys may be solution structured with other elements such as zinc, aluminum, nickel, iron, carbon, tin, silver, copper, titanium, rare earth elements, and the like, and any combination thereof. Degradable metal aluminum alloys may be solution structured with elements such as nickel, iron, carbon, tin, silver, copper, titanium, gallium, and the like, and any combination thereof.

In some embodiments, an alloy, such as a magnesium alloy or an aluminum alloy described herein has a dopant included therewith, such as during fabrication. For example, the dopant may be added to one of the alloying elements prior to mixing all of the other elements in the alloy. For example, during the fabrication of an AZ aluminum alloy, the dopant (e.g., zinc) may be dissolved in aluminum, followed by mixing with the remaining alloy, magnesium, and other components if present. Additional amounts of the aluminum may be added after dissolving the dopant, as well, without departing from the scope of the present disclosure, in order to achieve the desired composition. Suitable dopants for inclusion in the degradable metal alloy materials described herein may include, but are not limited to, iron, copper, nickel, gallium, carbon, tungsten, silver, and any combination thereof.

The dopant may be included with the magnesium and/or aluminum alloy degradable metal materials described herein in an amount of from about 0.05% to about 15% by weight of the degradable metal material, encompassing every value and subset therebetween. For example, the dopant may be present in an amount of from about 0.05% to about 3%, or about 3% to about 6%, or about 6% to about 9%, or about 9% to about 12%, or about 12% to about 15% by weight of the degradable metal material, encompassing every value and subset therebetween. Other examples include a dopant in an amount of from about 1% to about 10% by weight of the degradable metal material, encompassing every value and subset therebetween. Each of these values is critical to the embodiments of the present disclosure and may depend on a number of factors including, but not limited to, the type of magnesium and/or aluminum alloy selected, the desired rate of degradation, the wellbore environment, and the like, and any combination thereof.

As specific examples, the magnesium alloy degradable metal material may comprise a nickel dopant in the range of about 0.1% to about 6% (e.g., about 0.1%, about 0.5%, about 1%, about 2%, about 3%, about 4%, about 5%, about 6%) by weight of the alloy, encompassing any value and subset therebetween; a copper dopant in the range of about 6% to about 12% (e.g., about 6%, about 7%, about 8%, about 9%, about 10%, about 11%, about 12%) by weight of the alloy, encompassing any value and subset therebetween; and/or an iron dopant in the range of about 2% to about 6% (e.g., about 2%, about 3%, about 4%, about 5%, about 6%) by weight of the alloy, encompassing any value and subset therebetween. As described above, each of these values is critical to the embodiments of the present disclosure to at least affect the degradation rate of the magnesium alloy.

As specific examples, the aluminum alloy degradable metal material may comprise a copper dopant in the range of about 8% to about 15% (e.g., about 8%, about 9%, about 10%, about 11%, about 12%, about 13%, about 14%, about 15%) by weight of the alloy, encompassing any value and subset therebetween; a mercury dopant in the range of about 0.2% to about 4% (e.g., about 0.2%, about 0.5%, about 1%, about 2%, about 3%, about 4%) by weight of the alloy, encompassing any value and subset therebetween; a nickel dopant in the range of about 1% to about 7% (e.g., about 1%, about 2%, about 3%, about 4%, about 5%, about 6%, about 7%) by weight of the alloy, encompassing any value and subset therebetween; a gallium dopant in the range of about 0.2% to about 4% (e.g., about 0.2%, about 0.5%, about 1%, about 2%, about 3%, about 4%) by weight of the alloy, encompassing any value and subset therebetween; and/or an iron dopant in the range of about 2% to about 7% (e.g., about 2%, about 3%, about 4%, about 5%, about 6%, about 7%) by weight of the alloy, encompassing any value and subset therebetween. As described above, each of these values is critical to the embodiments of the present disclosure to at least affect the degradation rate of the aluminum alloy.

The degradable metal materials (e.g., magnesium and/or aluminum alloys) described herein may further comprise an amount of material, termed "supplementary material," that is defined as neither the primary alloy, other specific alloying materials forming the doped alloy, or the dopant. This supplementary material may include, but is not limited to, unknown materials, impurities, additives (e.g., those purposefully included to aid in mechanical properties), and any combination thereof. The supplementary material minimally, if at all, effects the acceleration of the corrosion rate of the doped alloy. Accordingly, the supplementary material may, for example, inhibit the corrosion rate or have no affect thereon. As defined herein, the term "minimally" with reference to the effect of the acceleration rate refers to an effect of no more than about 5% as compared to no supplementary material being present. This supplementary material may enter the degradable metal materials of the present disclosure due to natural carry-over from raw materials, oxidation of the degradable metal material or other elements, manufacturing processes (e.g., smelting processes, casting processes, alloying process, and the like), or the like, and any combination thereof. Alternatively, the supplementary material may be intentionally included additives placed in the degradable metal material to impart a beneficial quality thereto, such as a reinforcing agent, a corrosion retarder, a corrosion accelerant, a reinforcing agent (i.e., to increase strength or stiffness, including, but not limited to, a fiber, a particulate, a fiber weave, and the like, and combinations thereof), silicon, calcium, lithium, manganese, tin, lead, thorium, zirconium, beryllium, cerium, praseodymium, yttrium, and the like, and any combination thereof. Generally, the supplemental material is present in the degradable metal material described herein in an amount of less than about 10% by weight of the degradable metal material, including no supplemental material at all (i.e., 0%).

Examples of specific magnesium alloy degradable metal materials for use in the embodiments of the present disclosure may include, but are not limited to, a doped MG magnesium alloy, a doped WE magnesium alloy, a doped AZ magnesium alloy, a doped AM magnesium alloy, or a doped ZK magnesium alloy. As defined herein, a "doped MG magnesium alloy" is an alloy comprising at least magnesium, dopant, and optional supplemental material, as defined herein; a "doped WE magnesium alloy" is an alloy comprising at least a rare earth metal, magnesium, dopant, and optional supplemental material, as defined herein; a "doped AZ magnesium alloy" is an alloy comprising at least aluminum, zinc, magnesium, dopant, and optional supplemental material, as defined herein; a "doped AM magnesium" is an alloy comprising at least aluminum, manganese, magnesium, dopant, and optional supplemental material, as defined herein; and a "ZK magnesium alloy" is an alloy comprising at least zinc, zirconium, magnesium, dopant, and optional supplemental material, as defined herein.

The doped MG magnesium alloy comprises about 75% to about 99.95% of magnesium, about 0.05% to about 15% of dopant, and about 0% to about 10% of supplemental material, each by weight of the doped MG magnesium alloy. The doped WE magnesium alloy comprises about 60% to about 98.95% of magnesium, about 1% to about 15% of a rare earth metal or combination of rare earth metals, about 0.05% to about 15% of dopant, and about 0% to about 10% of supplemental material, each by weight of the doped WE magnesium alloy. The rare earth metal may be selected from the group consisting of scandium, lanthanum, cerium, praseodymium, neodymium, promethium, samarium, europium, gadolinium, dysprosium, holmium, erbium, thulium, ytterbium, lutetium, yttrium, and any combination thereof. The doped AZ magnesium alloy comprises about 57.3% to about 98.85% of magnesium, about 1% to about 12.7% of aluminum, about 0.05% to about 15% of dopant, and about 0% to about 10% of supplemental material, each by weight of the doped AZ magnesium alloy. The doped ZK magnesium alloy comprises about 58% to about 98.94% of magnesium, about 1% to about 12% of zinc, about 0.01% to about 5% of zirconium, about 0.05% to about 15% of dopant, and about 0% to about 10% of supplemental material, each by weight of the doped ZK magnesium alloy. The doped AM magnesium alloy comprises about 61% to about 97.85% of magnesium, about 2% to about 10% of aluminum, about 0.1% to about 4% of manganese, about 0.05% to about 15% of dopant, and about 0% to about 10% of supplemental material, each by weight of the doped AM magnesium alloy. Each of these values is critical to the embodiments of the present disclosure and may depend on a number of factors including, but not limited to, the desired degradation rate, the type of dopant(s) selected, the presence and type of supplemental material, and the like, and combinations thereof.

Examples of specific aluminum alloy degradable metal materials for use in the embodiments of the present disclosure may include, but are not limited to, a doped silumin aluminum alloy (also referred to simply as "a doped silumin alloy"), a doped Al—Mg aluminum alloy, a doped Al—Mg—Mn aluminum alloy, a doped Al—Cu aluminum alloy, a doped Al—Cu—Mg aluminum alloy, a doped Al—Cu—Mn—Si aluminum alloy, a doped Al—Cu—Mn—Mg aluminum alloy, a doped Al—Cu—Mg—Si—Mn aluminum alloy, a doped Al—Zn aluminum alloy, a doped Al—Cu—Zn aluminum alloy, and any combination thereof. As defined herein, a "doped silumin aluminum alloy" is an alloy comprising at least silicon, aluminum, dopant, and optional supplemental material, as defined herein; a "doped Al—Mg aluminum alloy" is an alloy comprising at least magnesium, aluminum, dopant, and optional supplemental material, as defined herein; a "doped Al—Mg—Mn aluminum alloy" is an alloy comprising at least magnesium, manganese, aluminum, dopant, and optional supplemental material, as defined herein; a "doped Al—Cu aluminum alloy" is an alloy comprising at least copper, aluminum, dopant, and optional supplemental material, as defined herein; a "doped Al—Cu—Mg aluminum alloy" is an alloy comprising at least copper, magnesium, aluminum, dopant, and optional supplemental material, as defined herein; a "doped Al—Cu—Mn—Si aluminum alloy" is an alloy comprising at least copper, manganese, silicon, aluminum, dopant, and optional supplemental material, as defined herein; a "doped Al—Cu—Mn—Mg aluminum alloy" is an alloy comprising at least copper, manganese, magnesium, aluminum, dopant, and optional supplemental material, as defined herein; a "doped Al—Cu—Mg—Si—Mn aluminum alloy" is an alloy comprising at least copper, magnesium, silicon, manganese, aluminum, dopant, and optional supplemental material, as defined herein; a "doped Al—Zn aluminum alloy" is an alloy comprising at least zinc, aluminum, dopant, and optional supplemental material, as defined herein; and a "doped Al—Cu—Zn aluminum alloy" is an alloy comprising at least copper, zinc, aluminum, dopant, and optional supplemental material, as defined herein.

The doped silumin aluminum alloy comprises about 62% to about 96.95% of aluminum, about 3% to about 13% silicon, about 0.05% to about 15% of dopant, and about 0% to about 10% of supplemental material, each by weight of the doped silumin aluminum alloy. The doped Al—Mg aluminum alloy comprises about 62% to about 99.45% of aluminum, about 0.5% to about 13% of magnesium, about 0.05% to about 15% of dopant, and about 0% to about 10% of supplemental material, each by weight of the doped Al—Mg aluminum alloy. The doped Al—Mg—Mn aluminum alloy comprises about 67% to about 99.2% of aluminum, about 0.5% to about 7% of magnesium, about 0.25% to about 1% of manganese, about 0.05% to about 15% of dopant, and about 0% to about 10% of supplemental material, each by weight of the doped Al—Mg—Mn aluminum alloy. The doped Al—Cu aluminum alloy comprises about 64% to about 99.85% of aluminum, about 0.1% to about 11% of copper, about 0.05% to about 15% of dopant, and about 0% to about 10% of supplemental material, each by weight of the doped Al—Cu aluminum alloy.

The doped Al—Cu—Mg aluminum alloy comprises about 61% to about 99.6% of aluminum, about 0.1% to about 13% of copper, about 0.25% to about 1% of magnesium, about 0.05% to about 15% of dopant, and about 0% to about 10% of supplemental material, each by weight of the doped Al—Cu—Mg aluminum alloy. The doped Al—Cu—Mn—Si aluminum alloy comprises about 68.25% to about 99.35% of aluminum, about 0.1% to about 5% of copper, about 0.25% to about 1% of manganese, about 0.25% to about 0.75% of silicon, about 0.05% to about 15% of dopant, and about 0% to about 10% of supplemental material, each by weight of the doped Al—Cu—Mn—Si aluminum alloy. The doped Al—Cu—Mn—Mg aluminum alloy comprises about 70.5% to about 99.35% of aluminum, about 0.1% to about 3% of copper, about 0.25% to about 0.75% of manganese, about 0.25% to about 0.75% of magnesium, about 0.05% to about 15% of dopant, and about 0% to about 10% of supplemental material, each by weight of the doped Al—Cu—Mn—Mg aluminum alloy. The doped Al—Cu—Mg—Si—Mn aluminum alloy comprises about 67.5% to about 99.49% of aluminum, about 0.5% to about 5% of copper, about 0.25% to about 2% of magnesium, about 0.1% to about 0.4% of silicon, about 0.01% to about 0.1% of manganese, about 0.05% to about 15% of dopant, and about 0% to about 10% of supplemental material, each by weight of the doped Al—Cu—Mg—Si—Mn aluminum alloy. The doped Al—Zn aluminum alloy comprises about 45% to about 84.95% of aluminum, about 15% to about 30% of zinc, about 0.05% to about 15% of dopant, and about 0% to about 10% of supplemental material, each by weight of the doped Al—Zn aluminum alloy. The doped Al—Cu—Zn aluminum alloy comprises about 63% to about 99.75% of aluminum, about 0.1% to about 10% of copper, about 0.1% to about 2% of zinc, about 0.05% to about 15% of dopant, and about 0% to about 10% of supplemental material, each by weight of the doped Al—Cu—Zn aluminum alloy.

In some embodiments, where at least two components of the wellbore isolation device are formed from a degradable metal material (e.g., a degradable magnesium and/or aluminum alloy), each component may comprise dissimilar metals that generate a galvanic coupling that either accelerates or decelerates the degradation rate of another component of the wellbore isolation device that is at least partially composed of a degradable substance, whether a degradable metal material or a degradable non-metal material (e.g., a degradable polymer), such as the packer element 220. As will be appreciated, such embodiments may depend on where the dissimilar metals lie on the galvanic series. In at least one embodiment, a galvanic coupling may be generated by embedding or attaching a cathodic substance or piece of material into an anodic component. For instance, the galvanic coupling may be generated by dissolving aluminum in gallium. A galvanic coupling may also be generated by using a sacrificial anode coupled to the degradable metal material. In such embodiments, the degradation rate of the degradable metal material may be decelerated until the sacrificial anode is dissolved or otherwise corroded away. As an example, the slips and buttons thereof or the mule shoe and the wear band may each be composed of a degradable metal material, and the slips and mule shoe may be a more electronegative material than the corresponding buttons and wear band. In such an embodiment, the galvanic coupling between the slips and buttons thereof or the mule shoe and the wear band may cause the slips and mule shoe to act as an anode and degrade before the buttons and wear band. Once the slips and mule shoe have degraded, the buttons and wear band would dissolve or degrade independently. Alternatively, the materials may be reversed so as to degrade the smaller components (i.e., the buttons and wear band more quickly).

In some embodiments, the packer element of the frac plug may be composed of a polymer (e.g., an elastomer) that is sufficiently resilient (i.e., elastic) to provide a fluid seal between two portions of a wellbore section. It may be desirable that the amount of degradation is capable of causing the packer element to no longer maintain a fluid seal in the wellbore capable of maintaining differential pressure. However, because the slips, the mule shoes, the buttons, the mandrel, the packer element, other components of a wellbore isolation device, or a combination thereof, are optionally additionally composed of a degradable material, the degradation of at least the three components may not necessitate that the packer element degrade to the point of breaking the fluid seal on its own. Similarly, it may be desirable that the packer element is composed of a degradable elastomer and, in some cases, degradation of the packer element may be desirably faster in rate than any other degradable components of the wellbore isolation device, such that fluid flow is restored in the wellbore even before further degradation results in a loss of structural integrity of the wellbore isolation device.

The degradation rate of the degradable polymer may be accelerated, rapid, or normal, as defined herein. Accelerated degradation may be in the range of from about 2 hours to about 36 hours, encompassing any value or subset therebetween. Rapid degradation may be in the range of from about 36 hours to about 14 days, encompassing any value or subset therebetween. Normal degradation may be in the range of from about 14 days to about 120 days, encompassing any value or subset therebetween. Accordingly, the degradation may be between about 120 minutes to about 120 days. For example, the degradation of the degradable polymer may be about 2 hours to about 30 days, or about 30 days to about 60 days, or about 60 days to about 90 days, or about 90 days to about 120 days, encompassing any value and subset therebetween. Each of these values is critical and depending on a number of factors including, but not limited to, the type of degradable polymer selected, the conditions of the wellbore environment, and the like.

The degradable polymer forming at least a portion of a component of the wellbore isolation device (e.g., the packer element 220) may be a material that is at least partially degradable in a wellbore environment including, but not limited to, a polyurethane rubber (e.g., cast polyurethanes, thermoplastic polyurethanes, polyethane polyurethanes); a polyester-based polyurethane rubber (e.g., lactone polyester-based thermoplastic polyurethanes); a polyether-based polyurethane rubber; a thiol-based polymer (e.g., 1,3,5,-triacryloylhexahydro-1,3,5-triazine); a thiol-epoxy polymer (e.g., having an epoxide functional group, such as bisphenol-A diglycidyl ether, triglycidylisocyanurate, and/or trimethylolpropane triglycidyl ether); a hyaluronic acid rubber; a polyhydroxobutyrate rubber; a polyester elastomer; a polyester amide elastomer; a starch-based resin (e.g., starch-poly(ethylene-co-vinyl alcohol), a starch-polyvinyl alcohol, a starch-polylactic acid, starch-polycaprolactone, starch-poly(butylene succinate), and the like); a polyethylene terephthalate polymer; a polyester thermoplastic (e.g., polyether/ester copolymers, polyester/ester copolymers); a polylactic acid polymer; a polybutylene succinate polymer; a polyhydroxy alkanoic acid polymer; a polybutylene terephthalate polymer; a polysaccharide; chitin; chitosan; a protein; an aliphatic polyester; poly(s-caprolactone); a poly(hydroxybutyrate); poly(ethyleneoxide); poly(phenyllactide); a poly(amino acid); a poly(orthoester); polyphosphazene; a polylactide; a polyglycolide; a poly(anhydride) (e.g., poly(adipic anhydride), poly(suberic anhydride), poly(sebacic anhydride), poly(dodecanedioic anhydride), poly(maleic anhydride), and poly(benzoic anhydride), and the like); a polyepichlorohydrin; a copolymer of ethylene oxide/polyepichlorohydrin; a terpolymer of epichlorohydrin/ethylene oxide/allyl glycidyl ether; copolymers thereof; terpolymers thereof; and any combination thereof.

In some embodiments, the degradable polymer may preferably be a polyurethane rubber, a polyester-based polyurethane rubber, or a polyether-based polyurethane rubber (collectively simply "polyurethane-based rubbers). These polyurethane-based rubbers degrade in water through a hydrolytic reaction, although other degradation methods may also affect the degradability of the polyurethane-based rubbers. As used herein, the term "hydrolytic reaction," and variants thereof (e.g., "hydrolytic degradation") refers to the degradation of a material by cleavage of chemical bonds in the presence of (e.g., by the addition of) an aqueous fluid. Polyurethane-based rubbers traditionally are formed by reacting a polyisocyanate with a polyol. In the embodiments described herein, although non-limiting, the polyol for forming a polyurethane-based rubber may be a natural oil polyol, a polyester polyol (e.g., polybutadienes (e.g., polybutanediol adipate), polycaprolactones, polycarbonates, and the like), or a polyether polyol (e.g., polytetramethylene ether glycol, polyoxypropylene-glycol, polyoxyethylene glycol, and the like). Because polyether polyols are typically hydrolytically more reactive than polyester polyols and natural oil polyols, polyether polyols may be preferred, particularly when the degradation of the degradable polymer is solely based on aqueous fluid contact and not additionally on other degradation stimuli. However, either polyol may be used to form the polyurethane-based rubber for use as the degradable polymer described herein, and each is critical to the disclosed embodiments, as the amount of desired degradation over time may depend on a number of factors including the conditions of the subterranean formation, the subterranean formation operation being performed, and the like. Combinations of these polyols may also be used, without departing from the scope of the present disclosure.

Accordingly, the rate of hydrolytic degradation of a polyurethane-based rubber for use as the degradable polymers described herein may be adjusted and controlled based on the order of the polyol addition, as well as the polyol properties and quantities. As an example, in some embodiments, the amount of polyol is included in an amount in the range of from about 0.25 to about 2 stoichiometric ratio of the polyisocyanate in the polyurethane-based rubber, encompassing any value and subset therebetween. For example, the polyol may be included in an amount of about 0.25 to about 0.5, or about 0.5 to about 1, or about 1 to about 1.5, or about 1.5 to about 2 stoichiometric ratio of the polyisocyanate in the polyurethane-based rubber, encompassing any value and subset therebetween. Each of these values is critical to the embodiments described herein and may depend on a number of factors including, but not limited to, the desired hydrolytic degradation rate, the type of polyol(s) selected, the wellbore environment, and the like.

In some embodiments, where the degradable polymer selected is a polyurethane-based rubber (e.g., for forming the packer element 220 and/or the frac ball 208), the inclusion of a low functionality initiator may impart flexibility thereto. Such low functionality initiators may include, but are not limited to, dipropylene glycol, glycerine, sorbitol/water solution, and any combination thereof. As used herein, the term "low functionality initiator," and grammatical variants thereof, refers to the average number of isocyanate reactive sites per molecule of in the range of from about 1 to about 5. These low functionality initiators impart flexibility to the packer element 220 and may be included in the polyurethane-based rubbers described herein in an amount in the range of from about 1% to about 50% by weight of the polyol in the polyurethane-based rubber, encompassing any value and subset therebetween. For example, the low functionality initiator(s) may be included in the polyurethane-based rubbers in an amount of about 1% to about 12.5%, or about 12.5% to about 25%, or about 25% to about 37.5%, or about 37.5% to about 50% by weight of the polyol in the polyurethane-based rubber, encompassing any value and subset therebetween. Additionally, in some embodiments, higher molecular weight polyols for use in forming the polyurethane-based rubbers described herein may impart flexibility to the packer element 220 described herein. For example, in some embodiments, the molecular weight of the selected polyols may be in the range of from about 200 Daltons (Da) to about 20000 Da, encompassing any value and subset therebetween. For example, the molecular weight of the polyols may be about 200 Da to about 5000 Da, or about 5000 Da to about 10000 Da, or about 10000 Da to about 15000 Da, or about 15000 Da to about 20000 Da, encompassing any value and subset therebetween. Each of these values is critical to the embodiments described herein and may depend on a number of factors including, but not limited to, the desired flexibility of the degradable polymer (and thus the component at least partially composed thereof), the type of subterranean formation operation being performed, the wellbore environment, and the like.

In some embodiments, the degradable polymer described herein may be formed from a thiol-based polymer. As used herein, the term "thiol" is equivalent to the term "sulfhydryl." The thiol-based polymer may comprise at least one thiol functional group. In some embodiments, the thiol-based polymer may comprise thiol functional groups in the range of from about 1 to about 22, encompassing every value and subset therebetween. For example, the thiol-based polymer may comprise thiol functional groups in an amount of about 1 to about 5, or 5 to about 10, or 10 to about 15, or 15 to about 20, or 20 to about 22, encompassing any value and subset therebetween. In other embodiments, the thiol-based polymer may comprise even a greater number of thiol functional groups. Each of these values is critical to the embodiments of the present disclosure and may depend on a number of factors including, but not limited to, the desired degradation rate, the desired degradation process, and the like.

The thiol-based polymer may be, but is not limited to, a thiol-ene reaction product, a thiol-yne reaction product, a thiol-epoxy reaction product, and any combination thereof. The thiol-based polymers, whether the reaction product of thiol-ene, thiol-yne, or thiol-epoxy, may be referred to herein as generally being the reaction product of a thiol functional group and an unsaturated functional group, and may be formed by click chemistry. The thiol functional group is an organosulfur compound that contains a carbon-bonded sulfhydryl, represented by the formula —C—SH or R—SH, where R represents an alkane, alkene, or other carbon-containing group of atoms.

Thiol-ene reactions may be characterized as the sulfur version of a hydrosilylation reaction. The thiol-ene reaction product may be formed by the reaction of at least one thiol functional group with a variety of unsaturated functional groups including, but not limited to, a maleimide, an acrylate, a norborene, a carbon-carbon double bond, a silane, a Michael-type nucleophilic addition, and any combination thereof. As used herein, the term "Michael-type nucleophilic addition," and grammatical variants thereof, refers to the nucleophilic addition of a carbanion or another nucleophile to an α,β-unsaturated carbonyl compound, having the general structure (O=C)—C$^\alpha$=C$^\beta$—. An example of a suitable thiol-ene reaction product may include, but is not limited to, 1,3,5,-triacryloylhexahydro-1,3,5-triazine. Examples of suitable thiol-ene/silane reaction products that may be used in forming at least a portion of the wellbore isolation device or component thereof include, but are not limited to, the following Formulas 1-6:

Formula 1

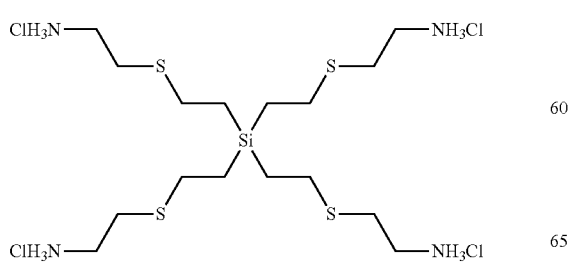

Formula 2

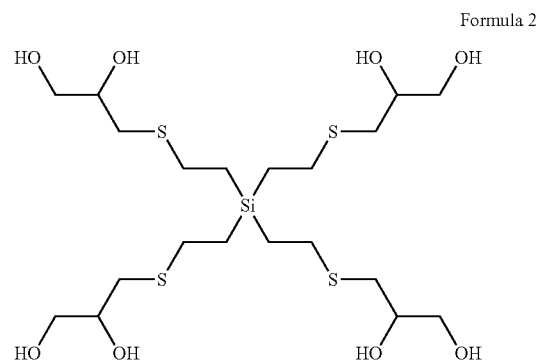

Formula 3

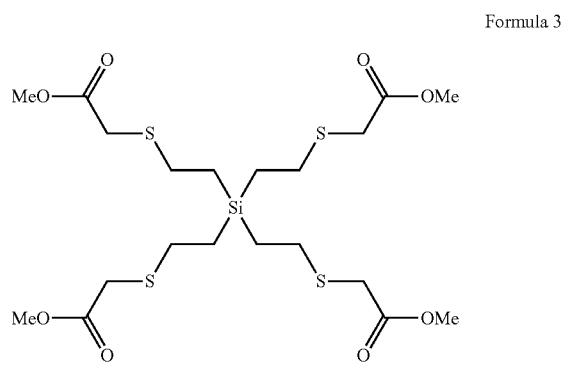

Formula 4

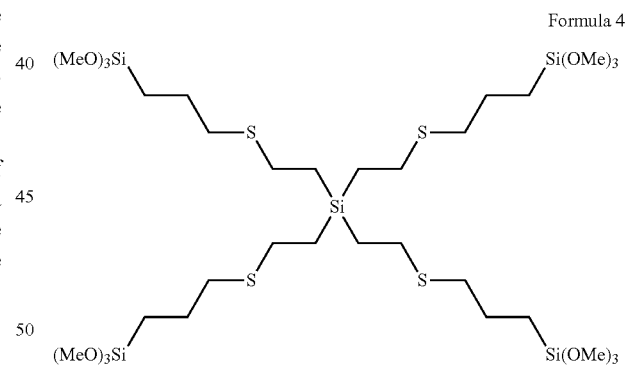

Formula 5

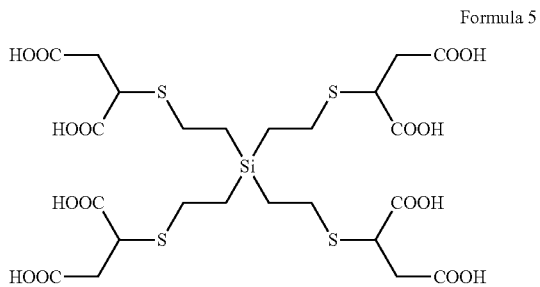

Formula 6

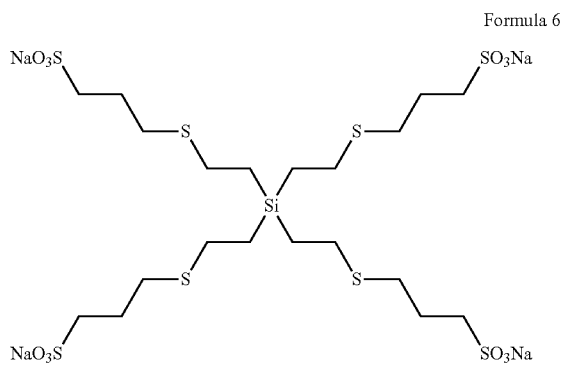

The thiol-yne reaction products may be characterized by an organic addition reaction between a thiol functional group and an alkyne, the alkyne being an unsaturated hydrocarbon having at least one carbon-carbon triple bond. The addition reaction may be facilitated by a radical initiator or UV irradiation and proceeds through a sulfanyl radical species. The reaction may also be amine-mediated, or transition-metal catalyzed.

The thiol-epoxy reaction products may be prepared by a thiol-ene reaction with at least one epoxide functional group. Suitable epoxide functional groups may include, but are not limited to, a glycidyl ether, a glycidyl amine, or as part of an aliphatic ring system. Specific examples of epoxide functional groups may include, but are not limited to, bisphenol-A diglycidyl ether, triglycidylisocyanurate, trimethylolpropane triglycidyl ether, and any combination thereof. The thiol-epoxy reaction products may proceed by one or more of the mechanisms presented below; however, other mechanisms may also be used without departing from the scope of the present disclosure:

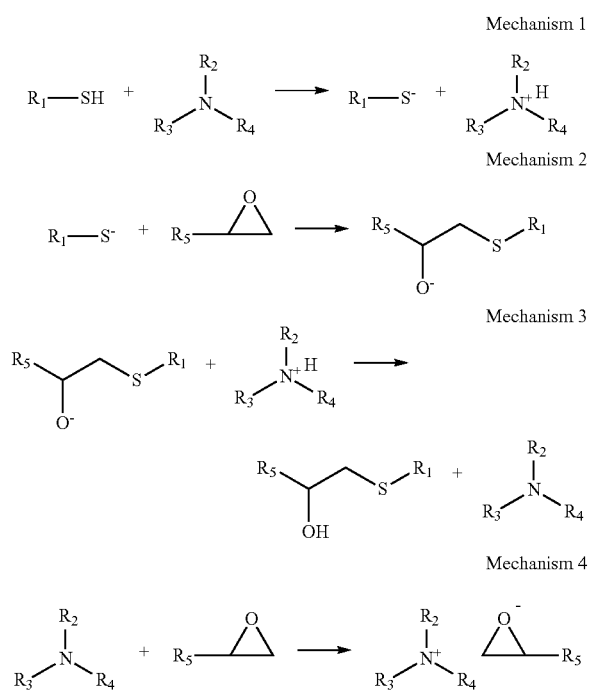

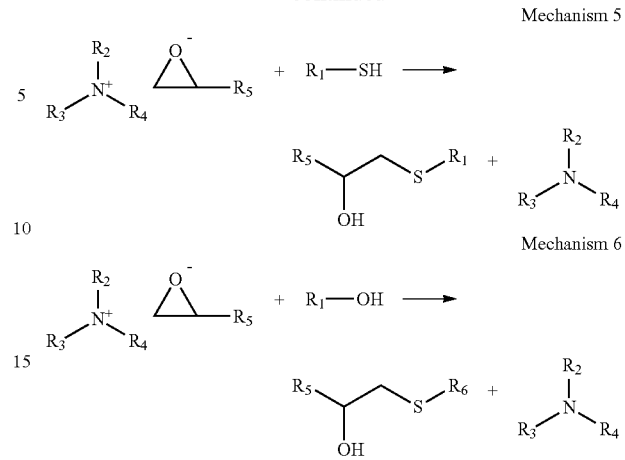

As mentioned above, the thiol-based polymer may comprise at least one thiol functional group and at least one degradable functional group. Such degradable functional groups may include, but are not limited to, one or more of a degradable monomer, a degradable oligomer, or a degradable polymer. Specific examples of degradable functional groups may include, but are not limited to, an acrylate, a lactide, a lactone, a glycolide, an anhydride, a lactam, an allyl, a polyethylene glycol, a polyethylene glycol-based hydrogel, an aerogel, a poly(lactide), a poly(glycolic acid), a poly(vinyl alcohol), a poly(N-isopropylacrylamide), a poly (s-caprolactone, a poly(hydroxybutyrate), a polyanhydride, an aliphatic polycarbonate, an aromatic polycarbonate, a poly(orthoester), a poly(hydroxyl ester ether), a poly(orthoester), a poly(amino acid), a poly(ethylene oxide), a polyphosphazene, a poly(phenyllactide), a poly(hydroxybutyrate), a dextran, a chitin, a cellulose, a protein, an aliphatic polyester, and any combination thereof.

In some embodiments, the thiol-based polymer comprises at least one polyethylene glycol-based hydrogel, such as one formed by a four-arm polyethylene glycol norbornene that is crosslinked with dithiol containing crosslinkers to form a chemically crosslinked hydrogel to impart swelling properties. The swelling properties of such a hydrogel may vary depending on a number of factors including, but not limited to, network density, the degree of crosslinking, and any combination thereof. In some embodiments, the degree of crosslinking may be desirably increased in order to achieve a higher tensile modulus and reduced swelling percentage.

The frac ball 208 may be composed of the degradable metal material or the degradable polymer described above. For example, the frac ball 208 may be made of polyglycolic acid (PGA) and/or polylactic acid (PLA). In other embodiments, the frac ball 208 or any other component may be comprised of a degradable material including, but not limited to, the degradable metal materials (e.g., the degradable magnesium and/or aluminum alloys) described above, the degradable polymers described above, a degradable glass, a dehydrated salt, and any combination thereof. That is, at least a portion of a single component may be composed of more than one degradable material, as described herein. Generally, the degradable metal material, the degradable glass material, and the dehydrated salts are rigid and provide structure, whereas the degradable polymer is resilient (i.e., elastic), which will dictate the particular components of the wellbore isolation device that are composed of either of these materials. Of course, variation in these materials may cause some to fall outside of this generalization, without departing from the scope of the present disclosure. Additionally, in other embodiments, any component of the wellbore isolation device may be a degradable non-metal material. Any non-degradable material (e.g., metals, plastics, glass, and the like) may additionally be used to form a component of the wellbore isolation device.

Examples of suitable degradable glass material may include, but are not limited to, glass polyalkenoate, borate glass polyalkenoate, calcium phosphate glass, polylactic acid/calcium phosphate glass, phosphate glass, silica glass, and any combination thereof. A dehydrated salt is suitable for use in the embodiments of the present disclosure if it will degrade over time as it hydrates. For example, a particulate solid anhydrous borate material that degrades over time may be suitable. Specific examples of particulate solid anhydrous borate materials that may be used include, but are not limited to, anhydrous sodium tetraborate (also known as anhydrous borax), and anhydrous boric acid. These anhydrous borate materials are only slightly soluble in water. However, with time and heat in a subterranean environment, the anhydrous borate materials react with the surrounding aqueous fluid and are hydrated. The resulting hydrated borate materials are highly soluble in water as compared to anhydrous borate materials and as a result degrade in the aqueous fluid. In some instances, the total time required for the anhydrous borate materials to degrade in an aqueous fluid is in the range of from about 8 hours to about 72 hours depending upon the temperature of the subterranean zone in which they are placed. Other examples include organic or inorganic salts like acetate trihydrate.

In some embodiments, the degradable polymer forming one or more components of the wellbore isolation device (e.g., the slips, the mule shoes, the buttons, the mandrel, the packer element, or other components of a wellbore isolation device) may have a thermoplastic polymer embedded therein. In some instances, the degradable polymer is itself a thermoplastic, in which case a different thermoplastic polymer may be embedded therein, in accordance with the embodiments described herein. That is, the thermoplastic material may serve as a polymer for forming one or more components of the wellbore isolation device alone or in combination, without departing from the scope of the present disclosure. The thermoplastic polymer may modify the strength, resiliency, or modulus of a component of the wellbore isolation device (e.g., the packer element 220) and may also control the degradation rate thereof. Suitable thermoplastic polymers may include, but are not limited to, polypropylene, an aliphatic polyester (e.g., polyglycolic acid, polylactic acid, polycaprolactone, polyhydroxyalkanoate, polyhydroxyalkanoiate, polyhydroxybutyrate, polyethylene adipate, polybutylene succinate, poly(lactic-co-glycolic) acid, poly(3-hydroxybutyrate-co-3-hyroxyvalerate, polycarbonate, and the like), and any combination thereof. In some situations, as stated above, the degradable substance may be a thermoplastic, which may be combined with one or more other degradable substances (in combination) or a thermoplastic listed above.

The amount of thermoplastic polymer that may be embedded in the degradable polymer is selected to confer a desirable quality (e.g., elasticity) without affecting the desired amount of degradation. In some embodiments, the thermoplastic polymer may be included in an amount in the range of from about 1% to about 91% by weight of the degradable polymer, encompassing any value or subset therebetween. For example, the thermoplastic polymer may be included in an amount of about 1% to about 25%, or about 25% to about 50%, or about 50% to about 75%, or about 75% to about 91% by weight of the degradable polymer, encompassing any value or subset therebetween. Each of these values is critical to the embodiments described herein and may depend on a number of factors including, but not limited to, the desired flexibility of the degradable polymer, the desired degradation rate of the degradable substance, the wellbore environment, and the like, and combinations thereof.

A reinforcing agent may additionally be included in the degradable polymer, which may increase the strength, stiffness, or creep resistance of the component of the wellbore isolation device comprising at least a portion of the degradable polymer. Such reinforcing agents may be a particulate, a fiber, a fiber weaver, and any combination thereof.

The particulate may be of any size suitable for embedding in the degradable polymer, such as in the range of from about 400 mesh to about 40 mesh, U.S. Sieve Series, and encompassing any value or subset therebetween. For example, the size of particulate for embedding in the degradable polymer may be in the range of about 400 mesh to about 300 mesh, or about 300 mesh to about 200 mesh, or about 200 mesh to about 100 mesh, or about 100 mesh to about 40 mesh, encompassing any value and subset therebetween. Moreover, there is no need for the particulates to be sieved or screened to a particular or specific particle mesh size or particular particle size distribution, but rather a wide or broad particle size distribution can be used, although a narrow particle size distribution is also suitable.

In some embodiments, the particulates may be substantially spherical or non-spherical. Substantially non-spherical proppant particulates may be cubic, polygonal, or any other non-spherical shape. Such substantially non-spherical particulates may be, for example, cubic-shaped, rectangular-shaped, rod-shaped, ellipse-shaped, cone-shaped, pyramid-shaped, planar-shaped, oblate-shaped, or cylinder-shaped. That is, in embodiments wherein the particulates are substantially non-spherical, the aspect ratio of the material may range such that the material is planar to such that it is cubic, octagonal, or any other configuration.

Particulates suitable for use as reinforcing agents in the embodiments described herein may comprise any material suitable for use in the degradable polymer that provides one or more of stiffness, strength, or creep resistance, or any other added benefit. Suitable materials for these particulates may include, but are not limited to, organophilic clay, silica flour, metal oxide, sand, bauxite, ceramic materials, glass materials, polymer materials (e.g., ethylene vinyl acetate or composite materials), polytetrafluoroethylene materials, nut shell pieces, cured resinous particulates comprising nut shell pieces, seed shell pieces, cured resinous particulates comprising seed shell pieces, fruit pit pieces, cured resinous particulates comprising fruit pit pieces, wood, composite particulates, and combinations thereof. Suitable composite particulates may comprise a binder and a filler material wherein suitable filler materials include silica, alumina, fumed carbon, carbon black, graphite, mica, titanium dioxide, barite, meta-silicate, calcium silicate, kaolin, talc, zirconia, boron, fly ash, hollow glass microspheres, solid glass, and combinations thereof.

The fibers for use as reinforcing agents in the degradable polymer may be of any size and material capable of being included therein. In some embodiments, the fibers may have a length of less than about 1.25 inches and a width of less than about 0.01 inches. In some embodiments, a mixture of different sizes of fibers may be used. Suitable fibers may be formed from any material suitable for use as a particulate, as described previously, as well as materials including, but not limited to, carbon fibers, carbon nanotubes, graphene, fullerene, a ceramic fiber, a plastic fiber, a glass fiber, a metal fiber, and any combination thereof. In some embodiments, the fibers may be woven together to form a fiber weave for use in the degradable polymer.

In some embodiments, the reinforcing agent may be included in the degradable polymer in an amount in the range of from about 1% to about 91% by weight of the degradable polymer, encompassing any value or subset therebetween. For example, the reinforcing agent may be included in an amount of about 1% to about 25%, or about 25% to about 50%, or about 50% to about 75%, or about 75% to about 91% by weight of the degradable polymer encompassing any value or subset therebetween. Each of these values is critical to the embodiments of the present disclosure and may depend on a number of factors including, but not limited to, the desired stiffness of the degradable polymer, the desired strength of the degradable polymer, the desired salt creep resistance of the degradable polymer, the type of degradable polymer selected, and the like, and any combination thereof.

According to an embodiment, each of the degradable substance(s) may include one or more tracers present therein. The tracer(s) can be, without limitation, radioactive, chemical, electronic, or acoustic. A tracer can be useful in determining real-time information on the rate of dissolution of the degradable substance. By being able to monitor the presence of the tracer, workers at the surface can make on-the-fly decisions that can affect the rate of dissolution of the remaining portions of the wellbore isolation device.

In some embodiments, the degradable substance may be at least partially encapsulated in a second material or "sheath" disposed on all or a portion of a given component of the wellbore isolation device. The sheath may be configured to help prolong degradation of the given component of the wellbore isolation device. The sheath may also serve to protect the component from abrasion within the wellbore. The sheath may be permeable, frangible (e.g., as discussed previously with regard to compressing the packer element against the casing or wall of the wellbore), or comprise a material that is at least partially removable at a desired rate within the wellbore environment. In either scenario, the sheath may be designed such that it does not interfere with the ability of the wellbore isolation device to form a fluid seal in the wellbore.

The sheath may comprise any material capable of use in a downhole environment and, depending on the component that the sheath encapsulates, the sheath may or may not be elastic such that it is able to expand with corresponding expansion of the component. For instance, a frangible sheath may break as the packer elements 220 expand to form a fluid seal by compressing against a casing or wall of a wellbore, whereas a permeable sheath may remain in place on the packer elements 220 as they form the fluid seal. As used herein, the term "permeable" refers to a structure that permits fluids (including liquids and gases) therethrough and is not limited to any particular configuration.

The sheath may comprise any of the afore-mentioned degradable substances. In some embodiments, the sheath may be made of a degradable substance that degrades at a rate that is faster than that of the underlying degradable substance that forms the component. Other suitable materials for the sheath include, but are not limited to, a TEFLON® coating, a wax, a drying oil, a polyurethane, an epoxy, a cross-linked partially hydrolyzed polyacrylic, a silicate material, a glass, an inorganic durable material, a polymer, polylactic acid, polyvinyl alcohol, polyvinylidene chloride, a hydrophobic coating, paint, and any combination thereof.

In some embodiments, all or a portion of the outer surface of a given component of the wellbore isolation device may be treated to impede degradation. For example, the outer surface of a given component may undergo a treatment that aids in preventing the degradable substance from degrading, or that aids in reducing the degradation rate. Suitable treatments may include, but are not limited to, an anodizing treatment, an oxidation treatment, a chromate conversion treatment, a dichromate treatment, a fluoride anodizing treatment, a hard anodizing treatment, and any combination thereof. As an example, an anodizing treatment may result in an anodized layer of material being deposited on the outer surface of a given component. The anodized layer may comprise materials such as, but not limited to, ceramics, metals, polymers, epoxies, elastomers, plastics, or any combination thereof and may be applied using any suitable processes known to those of skill in the art. Examples of suitable processes that result in an anodized layer include, but are not limited to, soft anodized coating, anodized coating, electroless nickel plating, hard anodized coating, ceramic coatings, carbide beads coating, plastic coating, thermal spray coating, high velocity oxygen fuel (HVOF) coating, a nano HVOF coating, and a metallic coating.

In some embodiments, all or a portion of the outer surface of a given component of the wellbore isolation device may be treated or coated with a substance configured to enhance degradation of the degradable material. For example, such a treatment or coating may be configured to remove a protective coating or treatment or otherwise accelerate the degradation of the degradable substance of the given component. An example is a degradable metal material coated with a layer of polyglycolic acid (PGA). In this example, the PGA would undergo hydrolysis and cause the surrounding fluid to become more acidic, which would accelerate the degradation of the underlying degradable metal material.

Embodiments described herein include, but are not limited to, Embodiments A-D.

Embodiment A is a method comprising: introducing a wellbore isolation device in an unset position into a wellbore penetrating a subterranean formation, the wellbore isolation device comprising a mandrel, slips disposed circumferentially about the mandrel and in a first position along the mandrel, and at least one packer element disposed in a second position along the mandrel, wherein the slips comprise particles coupled thereto forming a modified surface, and wherein the particles comprise sharp protrusions; actuating the wellbore isolation device from the unset position to a set position within the wellbore; frictionally engaging the modified surface of the slips with a wellbore surface when the wellbore isolation device is in the set position; and compressing the at least one packer element against the wellbore surface when the wellbore isolation device is in the set position.

Embodiment B is a wellbore isolation device comprising: a mandrel; slips disposed circumferentially about the mandrel and in a first position along the mandrel, wherein the slips comprise particles coupled thereto forming a modified surface, and wherein the particles comprise at least some sharp protrusions; and at least one packer element disposed along the mandrel and in a second position along the mandrel.

Embodiments A and B may optionally include at least one of the following: Element 1: wherein the slips comprise a button, and wherein the particles are coupled to the button;

Element 2: Element 1 and wherein the button comprises a degradable material; Element 3: wherein the particles are coupled directly to the slips; Element 4: wherein the slips are at least partially degradable; Element 5: wherein the modified surface is a first modified surface and the particles are first particles, wherein the wellbore isolation device further comprises a mule shoe secured to the mandrel at a terminal end of the wellbore isolation device, wherein the mule shoe comprises second particles coupled thereto forming a second modified surface, and wherein the second particles comprise smooth surfaces substantially absent of sharp protrusions; Element 6: Element 5 and wherein the second particles are coupled directly to the mule shoe; Element 7: Element 5 and wherein the mule shoe comprises a wear band having the second particles coupled thereto; Element 8: Element 7 and wherein the button is a first button, wherein the wear band is formed by second buttons coupled to the mule shoe, and wherein the second particles are coupled to the second buttons; Element 9: Element 7 and wherein the wear band encircles the mule shoe and the second particles are coupled directly to the wear band; and Element 10: Element 7 and wherein at least a portion of the wear band comprises a degradable material. Exemplary combination include, but are not limited to, Element 3 in combination with Element 1 and optionally Element 2; Element 4 in combination with Element 3; Element 4 in combination with Element 1 and optionally Element 3; one more of Elements 1-4 in combination with Element 5 and optionally one more of Elements 6-10; Element 5 in combination with Elements 6 an 7; Element 5 in combination with one or more of Elements 7-10; and the like.

Embodiment C is a wellbore isolation device comprising: a mandrel; slips disposed circumferentially about the mandrel and in a first position along the mandrel; at least one packer element disposed along the mandrel and in a second position along the mandrel; and a mule shoe secured to the mandrel at a lower end of the wellbore isolation device, wherein the mule shoe comprises particles coupled thereto forming a second modified surface, and wherein the particles comprise smooth surfaces substantially absent of sharp protrusions.

Embodiment C may optionally include at least one of the following: Element 11: wherein the particles are coupled directly to the mule shoe; Element 12: wherein the mule shoe comprises a wear band having the particles coupled thereto; Element 13: wherein at least a portion of the wear band comprises a degradable material; and Element 14: wherein the wear band is formed by buttons coupled to the mule shoe, and wherein the particles are coupled to the buttons. Exemplary combinations include, but are not limited to, Elements 12 and 13 in combination; Elements 11 and 12 in combination; Elements 11, 12, and 14 in combination and optionally in further combination with Element 13; and the like.

Embodiment D is a well system comprising a conveyance extending into a wellbore penetrating a subterranean formation with the wellbore isolation tool of Embodiment B or C coupled thereto at a distal end (i.e., the end in the wellbore) of the conveyance. Embodiment D may optionally include the Elements of Embodiments B or C described herein.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces.

The invention claimed is:

1. A method comprising:
   introducing a wellbore isolation device in an unset position into a wellbore penetrating a subterranean formation, the wellbore isolation device comprising a mandrel, slips disposed circumferentially about the mandrel and in a first position along the mandrel, and at least one packer element disposed in a second positon along the mandrel, wherein the slips comprise first particles coupled thereto forming a first modified surface, and wherein the particles comprise sharp protrusions; wherein the modified surface is a first modified surface and the particles are first particles, wherein the wellbore isolation device further comprises a mule shoe secured to the mandrel at a terminal end of the wellbore isolation device, wherein the mule shoe comprises second particles coupled thereto forming a second modified surface, and wherein the second particles comprise smooth surfaces substantially absent of sharp protrusions,
   actuating the wellbore isolation device from the unset position to a set position within the wellbore;
   frictionally engaging the first modified surface of the slips with a wellbore surface when the wellbore isolation device is in the set position; and
   compressing the at least one packer element against the wellbore surface when the wellbore isolation device is in the set position.

2. The method of claim 1, wherein the slips comprise a button, and wherein the first particles are coupled to the button.

3. The method of claim 2, wherein the button comprises a degradable material.

4. The method of claim 1, wherein the first particles are coupled directly to the slips.

5. The method of claim 1, wherein the slips are at least partially degradable.

6. The method of claim 1, wherein the second particles are coupled directly to the mule shoe.

7. The method of claim 1, wherein the mule shoe comprises a wear band having the second particles coupled thereto.

8. The method of claim 7, wherein the wear band is formed by buttons coupled to the mule shoe, and wherein the second particles are coupled to the buttons.

9. The method of claim 7, wherein the wear band encircles the mule shoe and the second particles are coupled directly to the wear band.

10. The method of claim 7, wherein at least a portion of the wear band comprises a degradable material.

11. A wellbore isolation device comprising:
   a mandrel;
   slips disposed circumferentially about the mandrel and in a first position along the mandrel, wherein the slips comprise first particles coupled thereto forming a first modified surface, and wherein the first particles comprise at least some sharp protrusions;
   a mule shoe secured to the mandrel at a lower end of the wellbore isolation device, wherein the mule shoe comprises second particles coupled thereto forming a second modified surface, and wherein the second particles comprise smooth surfaces substantially absent of sharp protrusions; and
   at least one packer element disposed along the mandrel and in a second position along the mandrel.

12. The wellbore isolation device of claim 11, wherein the slips comprise a button that comprises a degradable material, and wherein the first particles are coupled to the button.

13. The wellbore isolation device of claim 11, wherein the first particles are coupled directly to the slips.

14. The wellbore isolation device of claim 11, wherein the second particles are coupled directly to the mule shoe.

15. The wellbore isolation device of claim 11, wherein the mule shoe comprises a wear band having the second particles coupled thereto, and wherein at least a portion of the wear band comprises a degradable material.

16. A wellbore isolation device comprising:
   a mandrel;
   slips disposed circumferentially about the mandrel and in a first position along the mandrel;
   at least one packer element disposed along the mandrel and in a second position along the mandrel; and
   a mule shoe secured to the mandrel at a lower end of the wellbore isolation device, wherein the mule shoe comprises second particles coupled thereto forming a second modified surface, and wherein the second particles comprise smooth surfaces substantially absent of sharp protrusions.

17. The wellbore isolation device of claim 16, wherein the second particles are coupled directly to the mule shoe.

18. The wellbore isolation device of claim 16, wherein the mule shoe comprises a wear band having the second particles coupled thereto, and wherein at least a portion of the wear band comprises a degradable material.

* * * * *